United States Patent
Guerin et al.

(10) Patent No.: US 10,537,547 B2
(45) Date of Patent: Jan. 21, 2020

(54) COMPOSITIONS FAVORING WOUND REPAIR

(71) Applicant: UNIVERSITÉ LAVAL, Québec (CA)

(72) Inventors: Sylvain Guerin, Saint-Augustin-de-Desmaures (CA); Lucie Germain, Québec (CA); Karine Zaniolo, Québec (CA); Camille Couture, Québec (CA); Pascale Desjardins, Québec (CA)

( * ) Notice: Subject to any disclaimer, the term of this patent is extended or adjusted under 35 U.S.C. 154(b) by 0 days.

(21) Appl. No.: 15/773,306

(22) PCT Filed: Nov. 4, 2016

(86) PCT No.: PCT/CA2016/051287
§ 371 (c)(1),
(2) Date: May 3, 2018

(87) PCT Pub. No.: WO2017/075715
PCT Pub. Date: May 11, 2017

(65) Prior Publication Data
US 2018/0318252 A1    Nov. 8, 2018

Related U.S. Application Data

(60) Provisional application No. 62/251,339, filed on Nov. 5, 2015.

(51) Int. Cl.
| | |
|---|---|
| *A61K 31/353* | (2006.01) |
| *A61K 31/4155* | (2006.01) |
| *C07D 311/58* | (2006.01) |
| *C07D 405/06* | (2006.01) |
| *A61P 27/02* | (2006.01) |
| *A61P 17/02* | (2006.01) |
| *G01N 33/50* | (2006.01) |
| *A61K 31/4152* | (2006.01) |

(52) U.S. Cl.
CPC ........ *A61K 31/353* (2013.01); *A61K 31/4152* (2013.01); *A61K 31/4155* (2013.01); *A61P 17/02* (2018.01); *A61P 27/02* (2018.01); *C07D 311/58* (2013.01); *C07D 405/06* (2013.01); *G01N 33/5044* (2013.01)

(58) Field of Classification Search
CPC ............................. A61K 31/35; A61K 31/353
See application file for complete search history.

(56) References Cited

U.S. PATENT DOCUMENTS 5,449,794 A * 9/1995 Markonius ............. A61K 31/35
514/456

FOREIGN PATENT DOCUMENTS

| KR | 20100029672 | 3/2010 |
| WO | 9616719 | 6/1996 |

OTHER PUBLICATIONS

Gramatica et al. CAS: 167:67692, 2017.*
Tang et al. Br J. Pharmacol., 2014, 171(9):2440-56.*
Boisselier E, Salmon L, Ruiz J, Astruc D. How to very efficiently functionalize gold nanoparticles by "click" chemistry. Chem Commun (Camb). Nov. 30, 2008;(44):5788-90.
Carrier P, Deschambeault A, Talbot M, Giasson CJ, Auger FA, Guérin SL, Germain L. Characterization of wound reepithelialization using a new human tissue-engineered corneal wound healing model. Invest Ophthalmol Vis Sci. Apr. 2008;49(4):1376-85.
Greenhalgh, D. et al., « PDGF and FGF Stimulate Would Healing in the Genetically Diabetic Mouse ». American Journal of Pathology, Jun. 1990 (Jun. 1990), vol. 136, No. 6, pp. 12351246.
Pierce, G. F. et al., « Role of Platelet Derived Growth Factor in Would Healing ». Journal of Cellular Biochemistry, Apr. 1991, vol. 45, pp. 913-326.
Crump, N. T. et al., « Dynamic Acetylation fo all Lysine-4-trimethylated histone H3 is Evolutionarily Conserved and Medicated by p300/CBP ». Proceedings of the National Academy of Science. May 10, 2011, vol. 108 No. 19, pp. 7814-7819.
Jo, H. et al., « Small Molecule Induced Cystolic Activation of Protein Kinase Akt Rescues Ischemia-Elicited Neuronal Death ». Proceedings of the National Academy of Science, Jun. 26, 2012, vol. 109, No. 26, pp. 10581-10586.
Squarize, C. et al., « Accelerated Would Healing by mTOR Activation in Genetically Defined Mouse Models ». PLoS One, May 2010, vol. 5 No. 5, e10643, pp. 1-10.
Cao, L. et al., « Downregulation of PTEN at Corneal Wound Sties Accelerates Wound Healing through Increased Cell Migration ». Investigative Ophthalmology and Visual Science, Apr. 2011, vol. 52, No. 5, pp. 2272-2278.

(Continued)

*Primary Examiner* — Rei Tsang Shiao
(74) *Attorney, Agent, or Firm* — Norton Rose Fulbright Canada; Marie-Helene Rochon

(57) ABSTRACT

Disclosed are methods of favouring epithelial wound healing in a subject. Wounds suitable for this method include wounds located on the skin or in a cornea The methods comprise contacting a wound with an activator of an AKT pathway and/or an inhibitor of the MAPK pathway such as CREB inhibitors. Preferred compounds include SC-79, C646, curcumin, platelet-derived growth factor, 4'chloro-3-hydroxy-2-naphthanilide and fumonisin B. A model for wound healing is also disclosed. The model can be used to identify test compounds that are AKT activators or inhibitors of MAPK pathway, which are suitable to favoring epithelial wound healing.

10 Claims, 18 Drawing Sheets
Specification includes a Sequence Listing.

(56) References Cited

OTHER PUBLICATIONS

Liang, Q. et al., « Signaling by HGF and KGF in Corneal Epithetical Cells, Ras/MAP Kinase and Jak-STAT Pathways ». Investigative Ophthalmology and Visual Science, Jul. 1998, vol. 39, No. 8, pp. 1329-1338.

Couture, C. et al., « The Tissue-Engineered Human Cornea as a Model to Study the Contribution of the Intergin-medicated Signal Transduction Pathways Activated during Corneal Wound Healing ». 10th World Biomaterials Congress, Mar. 30, 2016.

Tummalapalli, B. et al., « Composite Wound Dressings of Pectin and Gelatin with Aloe Vera and Curcumin as Bioactive Agents ». International Journal of Biological Macromolecules, Jan. 2016, vol. 82, pp. 1047-1113.

Yang, H. et al., « Lucidone Promotes the Cutaneous Wound Healing Proces via Activation of the PI3K/AKT, Wnt/B-Catenin and NF-kB Signal Pathways ». Biochimica et Biophysica Acta, Nov. 2, 2016, vol. 1864, pp. 151-168.

Cursiefen et al.: "Nonvascular VEGF receptor 3 expression by corneal epithelium maintains avascularity and vision", PNAS, vol. 103, 2006, pp. 11405-11410.

Ambati et al.: "Corneal avascularity is due to soluble VEGF receptor-1", Nature, vol. 443, 2006, pp. 993-997.

Bikbova et al.: "Diabetic corneal neuropathy: clinical perspectives", Clinical Ophtalmology, vol. 2018, pp. 981-987.

Pan et al.: "Effect of VEGF on Corneal Nerve Growth and Corneal Wound Healing", Investigative Ophthalmology & Visual Science, vol. 53, 2012.

Couture et al.: "Enhanced wound healing of tissue-engineered human corneas through altered phosphorylation of the CREB and AKT signal transduction pathways", Acta Biomaterialia, vol. 73, 2018, pp. 312-325.

* cited by examiner

COMPOSITIONS FAVORING WOUND REPAIR

CROSS-REFERENCE TO RELATED APPLICATIONS AND DOCUMENTS

This application claims priority from U.S. provisional patent application 62/251,339 filed on Nov. 5, 2015. This application is filed concurrently with a sequence listing in an electronic format. The content of the priority application and the sequence listing is herewith incorporated in its entirety.

FIELD OF THE INVENTION

The present disclosure concerns therapeutic compositions for accelerating epithelial wound repair as well as methods for identifying compounds that can be used for accelerating epithelial wound repair.

BACKGROUND

Epithelial wound healing is a major health concern, especially when the wound is located in the skin or in the cornea. The cornea is localized at the outer surface of the eye. It is a transparent organ, highly specialized and unique that is continually subjected to abrasive forces and occasional mechanical or chemical trauma because of its anatomical localization. A complete reepithelialization and the reorganization of a mature smooth stratified epithelium, as well as a structured stroma, is essential in restoring the imaging properties of the cornea. Damages to the cornea that can be due in part to slow wound healing can result in scarring or opacification that may lead to visual defects and even complete loss of vision in which case corneal transplant is required.

Corneal wounds account for 14% of the medical consultations and 8% of hospitalization for ocular problems in the ophthalmology units of North America. They can be superficial, with damage limited to the epithelium, or associated with a deeper involvement of the epithelial basement membrane and the stroma. Approximately 75% of all ocular damages result from mechanical or abrasive damages. Chemical burns accounts for 5 to 22% of the ocular wounds and between 30 to 80% of them result from damages caused by alkaline compounds (ammonia, sodium hydroxide, chemical glues). In addition, severe recurrent and persistent corneal wounds are often secondary to ocular diseases such as trauma, herpetic infections and autoimmune diseases of the cornea. Despite available treatments, many of these wounds persist for weeks and months or else recur frequently and can progress to corneal perforation with a risk of eye loss. Furthermore, one million laser vision corrective procedures are performed each year using refractive surgery in USA. Photorefractive keratectomy (PRK) and laser in situ keratomileusis (LASIK) are the most common methods used for the correction of myopia, hyperopia, and astigmatism. However, because of the higher risk of complications, such as haze and pain postoperatively, as well as more unpredictable refractive results after the correction of high ametropias with PRK, LASIK has become the most popular corneal refractive surgery in the world. The cellular and molecular regulatory phenomena associated with postoperative wound healing are likely to be involved in the adverse effects after these surgeries but their underlying mechanisms have not yet been clearly elucidated. In fact, variability in wound healing is often a major factor involved in cases with overcorrection, undercorrection, stromal opacity, and other complications that occur with these surgeries in the treatment of either myopia or hyperopia. Moreover, 1.82 million cataract surgeries are performed in the USA annually, making it the most common surgical procedure performed by healthcare providers. Although cataract surgery initially yields a good restoration of vision, secondary visual loss results following a wound-healing response within the remaining lens tissue; this leads to cells the deformation of the underlying collagenous posterior capsule and in the deposition of additional matrix components which cause light scatter and to a visual deterioration known as posterior capsule opacification (PCO). Complications, primarily due to wound healing difficulties, occur in 0.4% of cataract surgeries.

There is thus a need to provide methods and tools for determining the usefulness of putative therapeutic agent to improve and accelerate wound healing. There is also a need to provide compounds and combinations of compounds for improving and accelerating wound healing, especially in the skin and the cornea.

SUMMARY

The present disclosure concerns that the activation of the AKT pathway and/or the inhibition of the MAPK pathway can accelerate the closure of an epithelial wound and thus favor healing of the epithelial wound. The present disclosure thus provides compounds capable of favoring healing of an epithelial wound as well as screening methods for identifying compounds capable of favoring healing of the epithelial wound.

According to a first aspect, the present disclosure concerns a method of favoring healing of an epithelial wound in a subject. Broadly, the method comprises contacting a wound healing efficient amount of a pharmaceutical composition with the wound, wherein the pharmaceutical composition comprises an activator of an AKT pathway and/or an inhibitor of a MAPK pathway in combination with a pharmaceutically acceptable carrier. In another embodiment, the pharmaceutical composition is applied topically in or near the epithelial wound. In an embodiment, the epithelial wound is located in a skin of the subject. In another embodiment, the epithelial wound is located in a cornea of the subject. In another embodiment, the activator of the AKT pathway is an Akt activator and can, for example, cause an increase or maintain the phosphorylation status of Akt. In still another embodiment, the Akt activator is SC-79. In still another embodiment, the inhibitor of the MAPK pathway is a CREB inhibitor and can, for example, cause an increase or maintain the dephosphorylation status of CREB. In still another embodiment, the CREB inhibitor is C646. In a further embodiment, the subject is a mammal such as, for example, a human.

According to a second aspect, the present disclosure concerns the use of a wound healing efficient amount of a pharmaceutical composition for favoring healing of an epithelial wound in a subject. Furthermore, the present disclosure concerns the use of a wound healing efficient amount of a pharmaceutical composition for the manufacture of a medicament for favoring healing of an epithelial wound in a subject. The pharmaceutical composition comprises an activator of an AKT pathway and/or an inhibitor of a MAPK pathway in combination with a pharmaceutically acceptable carrier. In another embodiment, the pharmaceutical composition is for topical administration in or near the epithelial wound or is formulated for topical administration in or near the epithelial wound. In an embodiment, the epithelial wound is located in a skin of the subject. In another embodiment, the epithelial wound is located in a cornea of the subject. In another embodiment, the activator AKT pathway is an Akt activator and can, for example, cause, increase or maintain the phosphorylation status of Akt. In still another embodiment, the Akt activator is SC-79. In still another embodiment, the inhibitor of the MAPK pathway is a CREB inhibitor and can, for example, cause, increase or maintain the dephosphorylation status of CREB. In still another embodiment, the CREB inhibitor is C646. In a further embodiment, the subject is a mammal such as, for example, a human.

According to a third aspect, the present disclosure concerns a pharmaceutical composition for favoring healing of an epithelial wound in a subject, said pharmaceutical composition comprising an activator of an AKT pathway and/or an inhibitor of a MAPK pathway in combination with a pharmaceutically acceptable carrier. In another embodiment, the pharmaceutical composition is for topical administration in or near the epithelial wound or is formulated for topical administration in or near the epithelial wound. In an embodiment, the epithelial wound is located in a skin of the subject. In another embodiment, the epithelial wound is located in a cornea of the subject. In another embodiment, the activator AKT pathway is an Akt activator and can, for example, cause an increase or maintain the phosphorylation status of Akt. In still another embodiment, the Akt activator is SC-79. In still another embodiment, the inhibitor of the MAPK pathway is a CREB inhibitor and can, for example, cause, an increase or maintain the dephosphorylation status of CREB. In still another embodiment, the CREB inhibitor is C646. In a further embodiment, the subject is a mammal such as, for example, a human.

According to a fourth aspect, the present disclosure concerns an activator of an AKT pathway for favoring healing of an epithelial wound in a subject, wherein the activator of the AKT pathway is optionally used with an inhibitor of a MAPK pathway. In another embodiment, the activator of the AKT pathway is for topical administration in or near the epithelial wound or is formulated for topical administration in or near the epithelial wound. In an embodiment, the epithelial wound is located in a skin of the subject. In another embodiment, the epithelial wound is located in a cornea of the subject. In another embodiment, the activator AKT pathway is an Akt activator and can, for example, cause an increase or maintain the phosphorylation status of Akt. In still another embodiment, the Akt activator is SC-79. In still another embodiment, the inhibitor of the MAPK pathway is a CREB inhibitor and can, for example, cause, an increase or maintain the dephosphorylation status of CREB. In still another embodiment, the CREB inhibitor is C646. In a further embodiment, the subject is a mammal such as, for example, a human.

According to a fifth aspect, the present disclosure concerns an inhibitor of a MAPK pathway for favoring healing of an epithelial wound in a subject, wherein the inhibitor of the MAPK pathway is optionally used with an activator of an AKT pathway. In another embodiment, the inhibitor of the MAPK pathway is for topical administration in or near the epithelial wound or is formulated for topical administration in or near the epithelial wound. In an embodiment, the epithelial wound is located in a skin of the subject. In another embodiment, the epithelial wound is located in a cornea of the subject. In another embodiment, the activator of the AKT pathway is an Akt activator and can, for example, cause an increase or maintain the phosphorylation status of Akt. In still another embodiment, the Akt activator is SC-79. In still another embodiment, the inhibitor of the MAPK pathway is a CREB inhibitor and can, for example, cause an increase or maintain the dephosphorylation status of CREB. In still another embodiment, the CREB inhibitor is C646. In a further embodiment, the subject is a mammal such as, for example, a human.

According to a sixth aspect, the present disclosure concerns a combination of an activator of an AKT pathway and an inhibitor of a MAPK pathway for favoring healing of an epithelial wound in a subject. In another embodiment, the combination is for topical administration in or near the epithelial wound or is formulated for topical administration in or near the epithelial wound. In an embodiment, the epithelial wound is located in a skin of the subject. In another embodiment, the epithelial wound is located in a cornea of the subject. In another embodiment, the activator of the AKT pathway is an Akt activator and can, for example, cause an increase or maintain the phosphorylation status of Akt. In still another embodiment, the Akt activator is SC-79. In still another embodiment, the inhibitor of the MAPK pathway is a CREB inhibitor and can, for example, cause an increase or maintain the dephosphorylation status of CREB. In still another embodiment, the CREB inhibitor is C646. In a further embodiment, the subject is a mammal such as, for example, a human.

According to a seventh aspect, the present disclosure concerns a pharmaceutical composition comprising the activator, the inhibitor or the combination defined herein and a pharmaceutically acceptable carrier.

According to an eight aspect, the present disclosure concerns a method for determining the usefulness of a test compound to favor epithelial wound healing. Broadly, the method comprises (a) contacting the test compound with a first epithelial cell to obtain a treated epithelial cell; (b) determining, in the treated epithelial cell, if the test compound activates the AKT pathway and/or inhibits the MAPK pathway; and (c) characterizing the test compound as useful for favoring wound healing when it is determined that the test compound activates, in the treated epithelial cell, the AKT pathway and/or inhibits, in the treated epithelial cell, the MAPK pathway. In an embodiment, the method comprises determining if the test compound activates Akt to determine if the test compound activates the AKT pathway. In still another embodiment, the method further comprises determining if the test compound causes, increases or maintains the phosphorylation status of Akt to determine if the test compound activates the AKT pathway. In an embodiment, the method comprises determining if the test compounds inhibits CREB to determine if the test compound inhibits the MAPK pathway. In still another embodiment, the method further comprises determining if the test compound causes, increases of maintains the dephosphorylation status of CREB to determine if the test compound inhibits the MAPK pathway. In an embodiment, the epithelial cell is a skin keratinocyte (and in still another embodiment, a human skin keratinocyte). In yet another embodiment, the epithelial cell is a corneal epithelial cell (and in still another embodiment, a human corneal epithelial cell) which can be, for example, located in an in vitro cornea model. In still another embodiment, the in vitro cornea model comprises cultured keratocytes (for example cultured human keratocytes), cultured epithelial corneal cells (for example human epithelial corneal cells) and an extracellular matrix substantially produced by the cultured keratocytes and the cultured epithelial corneal cells. In yet another embodiment, the epithelium of the in vitro cornea is wounded before step (a) and the method further comprises determining the rate of closure of the wound in the presence of the test compound to confirm the usefulness of the test compound in favoring wound healing. In a further embodiment, the in vitro cornea further comprises a second reconstructed stroma comprising cultured keratocytes (for example comprising human cultured keratocytes) and the extracellular matrix substantially produced by the cultured keratocytes placed on one side of the wound to provide support for the reepithelialization of the wound.

According to a ninth aspect, the present disclosure provides an in vitro model for screening for the ability of a test compound or a combination of test compounds to increase the closure of a wound, said in vitro cornea model comprising cultured keratocytes (for example cultured human keratocytes) forming a first reconstructed stroma, cultured epithelial corneal cells (for example cultured human epithelial corneal cells) seeded on the first reconstructed stroma and an extracellular matrix substantially produced by the cultured keratocytes and the cultured epithelial corneal cells. In an embodiment, an epithelial wound has been made to the in vitro cornea model. In still another embodiment, the in vitro model further comprises a second reconstructed stroma comprising cultured keratocytes and the extracellular matrix substantially produced by the cultured keratocytes placed on one side of the wound to provide support for the reepithelialization of the epithelial wound.

BRIEF DESCRIPTION OF THE DRAWINGS

Having thus generally described the nature of the invention, reference will now be made to the accompanying drawings, showing by way of illustration, a preferred embodiment thereof, and in which.

DETAILED DESCRIPTION

Figure 1:
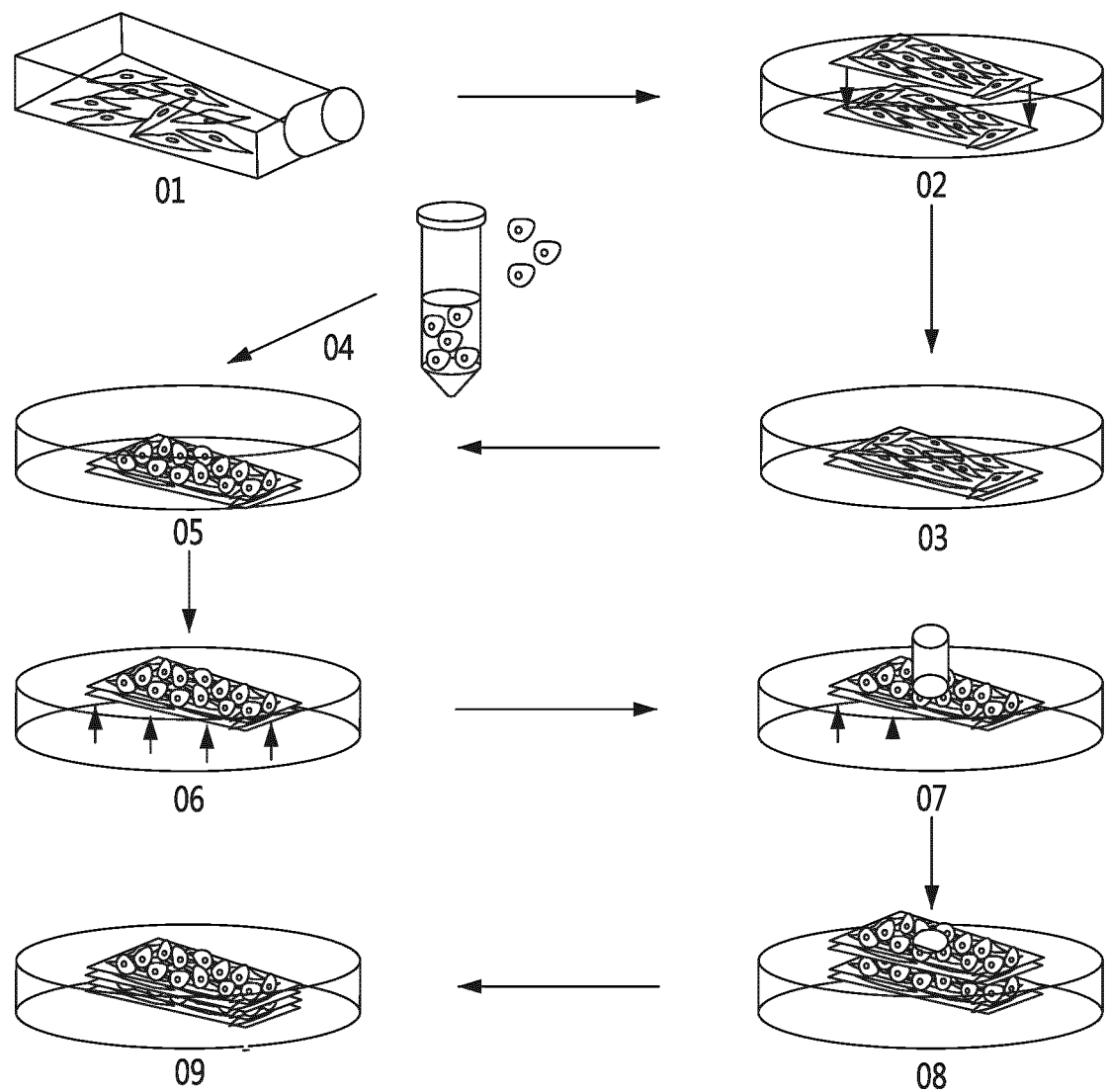
FIG. 1 illustrates the process for making and using an embodiment of the in vitro human cornea model used in the Examples. Briefly, human stromal fibroblasts are cultured in the presence of ascorbic acid during 40 days to allow the production of a handleable fibroblast tissue sheet (step 01). Then two fibroblasts tissue sheets are superimposed (step 02) and further cultured for at least 7 days to allow the formation of a self-assembled stromal matrix (step 03). Human corneal epithelial cells are added (step 04) to the reconstructed stroma and cultured submersed in the culture medium to form a tissue-engineered cornea (step 05). The tissue-engineered cornea is raised at the air-liquid interface and cultured for an additional 7 days to allow the maturation of the epithelium (step 06). The tissue engineered cornea is then wounded with a punch (step 07). A second stromal matrix is placed under the wounded tissue-engineered cornea (step 08) to assist wound healing. Wound closure is then monitored 4 to 7 days (step 09). When present, the putative therapeutic agent can be added at any steps of the process illustrated herein, but preferably at steps 06, 07 or 08.

The present disclosure concerns compounds, combinations and methods for acceleration and thus favoring healing of an epithelial wound in a subject. The subject that can benefit from these compounds, combinations and methods can be a mammal, such as, for example, a human.

In context of the present disclosure, a "wound" refers to the pathological disruption of an epithelium. The wound can be caused or maintained by a mechanical stress (such as, for example, a puncture, a scratch, a punch, a suture), by a chemical stress, by an infection (such as, for example, a bacterial, a viral or a fungal infection), etc. In an embodiment, the wound can be an ulcer, a burnt area, a surgical wound, etc. The wound can breach the integrity of the epithelium of the cornea, of the skin, of the lung, the blood vessels, the lymphatic vessels, of glands, of kidney tubules, of the bronchi, of the uterus, of the digestive tract, of the bladder, of the trachea, of the respiratory tract, of the esophagus, of the mouth, of the vagina, of the urethra, of the ureter, etc.

As it will be shown below, the compounds, combinations and methods described herein favor the healing of a wound by accelerating wound healing. The expression "favoring the healing of a wound" refers to the ability of the compounds, the combinations and the methods described herein to accelerate the rate of wound closure, reduce a side-effect associated with an open wound or the healing of such wound (such as, for example, edema, infection, pain) and/or reduce pathological scarring (such as, for example, hypertrophic scarring, keloid scarring, etc.).

As shown herein, inhibitors of the MAPK signaling pathway, especially inhibitors of the cAMP response element binding protein (CREB) favor wound healing by accelerating the rate of wound closure. As such, the compounds, combinations and methods described herein can include inhibitors of the MAPK signaling pathway, especially inhibitors of the cAMP response element binding protein (CREB). CREB (cAMP response element-binding protein) is a calcium- and cAMP-regulated transcription factor. It binds to certain DNA sequences called cAMP response elements (CRE), thereby increasing or decreasing the transcription of the downstream genes. In the context of the present disclosure, the expressions "inhibitors of CREB" or "CREB inhibitor" refers to a compound or a combination of compounds capable of limiting, and in some embodiments inhibiting, the biological activity of CREB. For example, the CREB inhibitor can limit or inhibit the phosphorylation status of CREB, can limit or inhibit the association of CREB to the CRE elements, can limit or inhibit the association of CREB-binding protein (CBP) with CREB, etc.

The CREB inhibitors can be specific for CREB or can be non-specific and include other targets (provided that such non-specific CREB inhibitor favors wound healing). Exemplary CREB inhibitors include, but are not limited to, C646, SGC-CBP30 (also known as CREBBP/EP300-selective chemical probe), 4'-chloro-3-hydroxy-2-naphthanilide (CAS 92-78-4), PF-CBP1 (CAS 1962928-21-7), histone acetyltransferase inhibitor II or hai II (CAS 932749-62-7) and curcumin (also known as synthetic curcumin). In embodiments of the present disclosure, a single CREB inhibitor can be used. For example, the compounds and combinations can include a single CREB inhibitor from the following list: C646, SGC-CBP30, 4'-chloro-3-hydroxy-2-naphthanilide, PF-CBP1, hai II and curcumin. In another embodiment, at least two CREB inhibitors are used. For example, the compounds and combinations can include C646 and SGC-CBP30, C646 and 4'-chloro-3-hydroxy-2-naphthanilide, C646 and curcumin, SGC-CBP30 and 4'-chloro-3-hydroxy-2-naphthanilide, SGC-CBP30 and curcumin, C646 and hai II, 4'-chloro-3-hydroxy-2-naphthanilide and hai II, SGC-CBP30 and hai II, hai II and curcumin, SGC-CBP30 and C646, C646 and PF-CBP1, 4'-chloro-3-hydroxy-2-naphthanilide and PF-CBP1, PF-CBP1 and hai II, PF-CBP1 and curcumin or 4'-chloro-3-hydroxy-2-naphthanilide and curcumin. In still another embodiment, at least three CREB inhibitors are used. For examples, the compounds and combinations can include C646, SGC-CBP30 and 4'-chloro-3-hydroxy-2-naphthanilide; C646, SGC-CBP30 and curcumin; C646, 4'-chloro-3-hydroxy-2-naphthanilide and curcumin; C646, SGC-CBP30 and PF-CBP1; C646, SGC-CBP30 and PF-CBP1; C646, curcumin and PF-CBP1; C646, SGC-CBP30 and hai II; C646, SGC-CBP30 and hai II; C646, curcumin and hai II; C646, PF-CBP1 and hai II; SGC-CBP30, PF-CBP1 and hai II; 4'-chloro-3-hydroxy-2-naphthanilide, PF-CBP1 and hai II or curcumin, PF-CBP1 and hai II. In yet another embodiment, the CREB inhibitor of the compounds and combinations can include all of C646, SGC-CBP30, 4'-chloro-3-hydroxy-2-naphthanilide, PF-CBP1, hai II and curcumin.

In an embodiment, the CREB inhibitor is C646. C646 is known as an inhibitor for histone acetyltransferase, a selective p300, CBP, histone H3 and H4 inhibitor. Its chemical name is 4-[4-[[5-(4,5-Dimethyl-2-nitrophenyl)-2-furanyl] methylene]-4,5-dihydro-3-methyl-5-oxo-1H-pyrazol-1-yl] benzoic acid (CAS: 328968-36-1 and PubChem CID: 1285941). C646 has the following chemical formula:

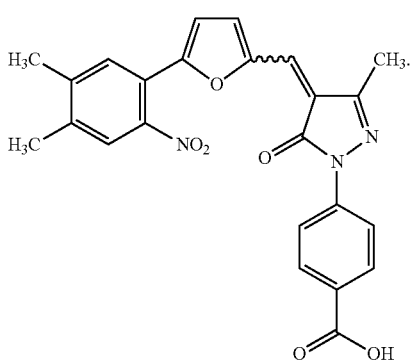 [SMILES: CC1=NN(c2ccc(C(=O)O)cc2)C(=O)C1=Cc1ccc(-c2cc(C)c(C)cc2[N+](=O)[O-])o1]

The CREB inhibitors can be used alone or in combination with other therapeutic agents known to favor wound healing. Such additional therapeutic agents include, without limitations, growth hormones and antibiotics. The additional therapeutic agents can be used simultaneously or in an alternate fashion with the CREB inhibitors. In an embodiment, the CREB inhibitors are used in combination with activators of the AKT signaling pathway.

The compounds, combinations and methods described herein can include activators of the AKT/PKB signaling pathway, especially activators of Akt. Also known as protein kinase B (PKB), Akt is a serine threonine-specific protein kinase. As shown herein, activators of the AKT/PKB signaling pathways, especially activators of Akt, favor wound healing by accelerating the rate of wound closure. In the context of the present disclosure, the expressions "activators of Akt" or "Akt activator" refer to a compound or a combination of compounds capable of increasing the biological activity of Akt. For example, the Akt activator can increase the affinity of Akt to its ligand, increase the kinase activity of Akt, etc.

The Akt activators can be specific for Akt or can be non-specific and include other targets (provided that such non-specific Akt activator favors wound healing). Exemplary Akt activators include, but are not limited to SC-79, platelet-derived growth factor (PDGF) and fumonisin B1. In an embodiment of the present disclosure, a single Akt activator is used. For example, the compounds and combinations can include a single Akt activator from the following list: SC-79, PDGF and fumonisin B1. In another embodiment, at least two Akt activators are used. For example, the compounds and combinations can include SC-79, and PDGF, SC-79 and fumonisin B1 or PDGF and fumonisin B. In still another embodiment, at least three Akt activators are used and include SC-79, PDGF and fumonisin B1.

In an embodiment, the Akt activator is SC-79. SC-79 is known as Akt kinase activator. SC-79 is an AKT activator. SC-79 binds to the plecktrin homology (PH) domain of Akt that mimics the binding of Ptdlns(3,4,5)P3 to induce a conformational change in Akt that enhances phosphorylation and activation. SC-79 induces cytosolic Akt signaling in cell based assays, and prevents neuronal death in a mouse model of stroke. Its chemical name is Ethyl-2-amino-6-chloro-4-(1-cyano-2-ethoxy-2-oxoethyl)-4H-chromene-3-carboxylate (CAS No: 305834-79-1). It has the following chemical formula:

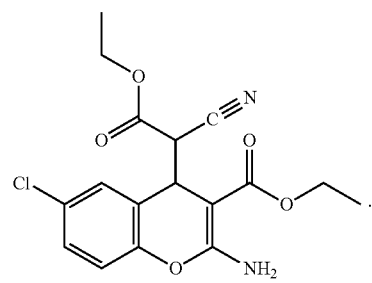 [SMILES: CCOC(=O)C1=C(N)Oc2ccc(Cl)cc2C1C(C#N)C(=O)OCC]

The Akt activators can be used alone or in combination with another therapeutic agent known to favor wound healing. Such additional therapeutic agents include, without limitations, growth hormones and antibiotics. The additional therapeutic agents can be used simultaneously or in an alternate fashion with the Akt activators. In an embodiment, the Akt activators can be used in combination with CREB inhibitors to favor wound healing.

The present disclosure also provides specific combinations of CREB inhibitors and Akt inhibitors to favor wound healing. Table 1 provide some combinations of CREB inhibitors that can be used to favor wound healing.

TABLE 1

Combinations of CREB inhibitors and Akt activators that can be used for favoring wound healing

| Combination | CREB inhibitor(s) | Akt activator(s) |
|---|---|---|
| 1 | C646 | SC-79 |
| 2 | SGC-CBP30 | SC-79 |
| 3 | 4'-chloro-3-hydroxy-2-naphthanilide | SC-79 |
| 4 | curcumin | SC-79 |
| 5 | PF-CBP1 | SC-79 |
| 6 | hai II | SC-79 |
| 7 | C646 | PDGF |
| 8 | SGC-CBP30 | PDGF |
| 9 | 4'-chloro-3-hydroxy-2-naphthanilide | PDGF |
| 10 | curcumin | PDGF |
| 11 | PF-CBP1 | PDGF |
| 12 | hai II | PDGF |
| 13 | C646 | fumonisin B1 |
| 14 | SGC-CBP30 | fumonisin B1 |
| 15 | 4'-chloro-3-hydroxy-2-naphthanilide | fumonisin B1 |
| 16 | curcumin | fumonisin B1 |
| 17 | PF-CBP1 | fumonisin B1 |
| 18 | hai II | fumonisin B1 |
| 19 | C646 and SGC-CBP30 | SC-79 |
| 20 | C646 and 4'-chloro-3-hydroxy-2-naphthanilide | SC-79 |

TABLE 1-continued

Combinations of CREB inhibitors and Akt activators that can be used for favoring wound healing

| Combination | CREB inhibitor(s) | Akt activator(s) |
|---|---|---|
| 21 | C646 and curcumin | SC-79 |
| 22 | SGC-CBP30 and 4'-chloro-3-hydroxy-2-naphthanilide | SC-79 |
| 23 | 4'-chloro-3-hydroxy-2-naphthanilide and curcumin | SC-79 |
| 24 | C646 and PF-CBP1 | SC-79 |
| 25 | C646 and hai II | SC-79 |
| 26 | SGC-CBP30 and PF-CBP1 | SC-79 |
| 27 | SGC-CBP30 and hai II | SC-79 |
| 28 | 4'-chloro-3-hydroxy-2-naphthanilide and PF-CBP1 | SC-79 |
| 29 | 4'-chloro-3-hydroxy-2-naphthanilide and hai II | SC-79 |
| 30 | curcumin and PF-CBP1 | SC-79 |
| 31 | curcumin and hai II | SC-79 |
| 32 | C646 and SGC-CBP30 | PDGF |
| 33 | C646 and 4'-chloro-3-hydroxy-2-naphthanilide | PDGF |
| 34 | C646 and curcumin | PDGF |
| 35 | SGC-CBP30 and 4'-chloro-3-hydroxy-2-naphthanilide | PDGF |
| 36 | 4'-chloro-3-hydroxy-2-naphthanilide and curcumin | PDGF |
| 37 | C646 and PF-CBP1 | PDGF |
| 38 | C646 and hai II | PDGF |
| 39 | SGC-CBP30 and PF-CBP1 | PDGF |
| 40 | SGC-CBP30 and hai II | PDGF |
| 41 | 4'-chloro-3-hydroxy-2-naphthanilide and PF-CBP1 | PDGF |
| 42 | 4'-chloro-3-hydroxy-2-naphthanilide and hai II | PDGF |
| 43 | curcumin and PF-CBP1 | PDGF |
| 44 | curcumin and hai II | PDGF |
| 45 | C646 and SGC-CBP30 | fumonisin B1 |
| 46 | C646 and 4'-chloro-3-hydroxy-2-naphthanilide | fumonisin B1 |
| 47 | C646 and curcumin | fumonisin B1 |
| 48 | SGC-CBP30 and 4'-chloro-3-hydroxy-2-naphthanilide | fumonisin B1 |
| 49 | 4'-chloro-3-hydroxy-2-naphthanilide and curcumin | fumonisin B1 |
| 50 | C646 and PF-CBP1 | fumonisin B1 |
| 51 | C646 and hai II | fumonisin B1 |
| 52 | SGC-CBP30 and PF-CBP1 | fumonisin B1 |
| 53 | SGC-CBP30 and hai II | fumonisin B1 |
| 54 | 4'-chloro-3-hydroxy-2-naphthanilide and PF-CBP1 | fumonisin B1 |
| 55 | 4'-chloro-3-hydroxy-2-naphthanilide and hai II | fumonisin B1 |
| 56 | curcumin and PF-CBP1 | fumonisin B1 |
| 57 | curcumin and hai II | fumonisin B1 |
| 58 | C646, SGC-CBP30 and 4'-chloro-3-hydroxy-2-naphthanilide | SC-79 |
| 59 | C646, SGC-CBP30 and curcumin | SC-79 |
| 60 | C646, SGC-CBP30 and PF-CBP1 | SC-79 |
| 61 | C646, SGC-CBP30 and hai II | SC-79 |
| 62 | SGC-CBP30, 4'-chloro-3-hydroxy-2-naphthanilide and curcumin | SC-79 |
| 63 | SGC-CBP30, 4'-chloro-3-hydroxy-2-naphthanilide and PF-CBP1 | SC-79 |
| 64 | SGC-CBP30, 4'-chloro-3-hydroxy-2-naphthanilide and hai II | SC-79 |
| 65 | C646, PF-CBP1 and hai II | SC-79 |
| 66 | SGC-CBP30, PF-CBP1 and hai II | SC-79 |
| 67 | 4'-chloro-3-hydroxy-2-naphthanilide, PF-CBP1 and hai II | SC-79 |
| 68 | curcumin, PF-CBP1 and hai II | SC-79 |
| 69 | C646, SGC-CBP30 and 4'-chloro-3-hydroxy-2-naphthanilide | PDGF |
| 70 | C646, SGC-CBP30 and curcumin | PDGF |
| 71 | C646, SGC-CBP30 and PF-CBP1 | PDGF |
| 72 | C646, SGC-CBP30 and hai II | PDGF |
| 73 | SGC-CBP30, 4'-chloro-3-hydroxy-2-naphthanilide and curcumin | PDGF |
| 74 | SGC-CBP30, 4'-chloro-3-hydroxy-2-naphthanilide and PF-CBP1 | PDGF |
| 75 | SGC-CBP30, 4'-chloro-3-hydroxy-2-naphthanilide and hai II | PDGF |
| 76 | C646, PF-CBP1 and hai II | PDGF |
| 77 | SGC-CBP30, PF-CBP1 and hai II | PDGF |
| 78 | 4'-chloro-3-hydroxy-2-naphthanilide, PF-CBP1 and hai II | PDGF |
| 79 | curcumin, PF-CBP1 and hai II | PDGF |
| 80 | C646, SGC-CBP30 and 4'-chloro-3-hydroxy-2-naphthanilide | fumonisin B1 |
| 81 | C646, SGC-CBP30 and curcumin | fumonisin B1 |

TABLE 1-continued

Combinations of CREB inhibitors and Akt activators that can be used for favoring wound healing

| Combination | CREB inhibitor(s) | Akt activator(s) |
|---|---|---|
| 82 | C646, SGC-CBP30 and PF-CBP1 | fumonisin B1 |
| 83 | C646, SGC-CBP30 and hai II | fumonisin B1 |
| 84 | SGC-CBP30, 4'-chloro-3-hydroxy-2-naphthanilide and curcumin | fumonisin B1 |
| 85 | SGC-CBP30, 4'-chloro-3-hydroxy-2-naphthanilide and PF-CBP1 | fumonisin B1 |
| 86 | SGC-CBP30, 4'-chloro-3-hydroxy-2-naphthanilide and hai II | fumonisin B1 |
| 87 | C646, PF-CBP1 and hai II | fumonisin B1 |
| 88 | SGC-CBP30, PF-CBP1 and hai II | fumonisin B1 |
| 89 | 4'-chloro-3-hydroxy-2-naphthanilide, PF-CBP1 and hai II | fumonisin B1 |
| 90 | curcumin, PF-CBP1 and hai II | fumonisin B1 |
| 91 | C646, SGC-CBP30, 4'-chloro-3-hydroxy-2-naphthanilide and curcumin | SC-79 |
| 92 | C646, SGC-CBP30, 4'-chloro-3-hydroxy-2-naphthanilide and PF-CBP1 | SC-79 |
| 93 | C646, SGC-CBP30, 4'-chloro-3-hydroxy-2-naphthanilide and hai II | SC-79 |
| 94 | C646, SGC-CBP30, PF-CBP1 and curcumin | SC-79 |
| 95 | C646, SGC-CBP30, hai II and curcumin | SC-79 |
| 96 | C646, PF-CBP1, 4'-chloro-3-hydroxy-2-naphthanilide and curcumin | SC-79 |
| 97 | C646, hai II, 4'-chloro-3-hydroxy-2-naphthanilide and curcumin | SC-79 |
| 98 | PF-CBP1, SGC-CBP30, 4'-chloro-3-hydroxy-2-naphthanilide and curcumin | SC-79 |
| 99 | hai II, SGC-CBP30, 4'-chloro-3-hydroxy-2-naphthanilide and curcumin | SC-79 |
| 100 | C646, SGC-CBP30, 4'-chloro-3-hydroxy-2-naphthanilide and curcumin | PDGF |
| 101 | C646, SGC-CBP30, 4'-chloro-3-hydroxy-2-naphthanilide and PF-CBP1 | PDGF |
| 102 | C646, SGC-CBP30, 4'-chloro-3-hydroxy-2-naphthanilide and hai II | PDGF |
| 103 | C646, SGC-CBP30, PF-CBP1 and curcumin | PDGF |
| 104 | C646, SGC-CBP30, hai II and curcumin | PDGF |
| 105 | C646, PF-CBP1, 4'-chloro-3-hydroxy-2-naphthanilide and curcumin | PDGF |
| 106 | C646, hai II, 4'-chloro-3-hydroxy-2-naphthanilide and curcumin | PDGF |
| 107 | PF-CBP1, SGC-CBP30, 4'-chloro-3-hydroxy-2-naphthanilide and curcumin | PDGF |
| 108 | hai II, SGC-CBP30, 4'-chloro-3-hydroxy-2-naphthanilide and curcumin | PDGF |
| 109 | C646, SGC-CBP30, 4'-chloro-3-hydroxy-2-naphthanilide and curcumin | fumonisin B1 |
| 110 | C646, SGC-CBP30, 4'-chloro-3-hydroxy-2-naphthanilide and PF-CBP1 | fumonisin B1 |
| 111 | C646, SGC-CBP30, 4'-chloro-3-hydroxy-2-naphthanilide and hai II | fumonisin B1 |
| 112 | C646, SGC-CBP30, PF-CBP1 and curcumin | fumonisin B1 |
| 113 | C646, SGC-CBP30, hai II and curcumin | fumonisin B1 |
| 114 | C646, PF-CBP1, 4'-chloro-3-hydroxy-2-naphthanilide and curcumin | fumonisin B1 |
| 115 | C646, hai II, 4'-chloro-3-hydroxy-2-naphthanilide and curcumin | fumonisin B1 |
| 116 | PF-CBP1, SGC-CBP30, 4'-chloro-3-hydroxy-2-naphthanilide and curcumin | fumonisin B1 |
| 117 | hai II, SGC-CBP30, 4'-chloro-3-hydroxy-2-naphthanilide and curcumin | fumonisin B1 |
| 118 | C646 | SC-79 and PDGF |
| 119 | C646 | SC-79 and fumonisin B1 |
| 120 | C646 | PDGF and fumonisin B1 |
| 121 | SGC-CBP30 | SC-79 and PDGF |
| 122 | SGC-CBP30 | SC-79 and fumonisin B1 |
| 123 | SGC-CBP30 | PDGF and fumonisin B1 |
| 124 | 4'-chloro-3-hydroxy-2-naphthanilide | SC-79 and PDGF |
| 125 | 4'-chloro-3-hydroxy-2-naphthanilide | SC-79 and fumonisin B1 |
| 126 | 4'-chloro-3-hydroxy-2-naphthanilide | PDGF and fumonisin B1 |
| 127 | curcumin | SC-79 and PDGF |
| 128 | curcumin | SC-79 and fumonisin B1 |
| 129 | curcumin | PDGF and fumonisin B1 |
| 130 | PF-CBP1 | SC-79 and PDGF |
| 131 | PF-CBP1 | SC-79 and fumonisin B1 |

TABLE 1-continued

Combinations of CREB inhibitors and Akt activators that can be used for favoring wound healing

| Combination | CREB inhibitor(s) | Akt activator(s) |
|---|---|---|
| 132 | PF-CBP1 | PDGF and fumonisin B1 |
| 133 | hai II | SC-79 and PDGF |
| 134 | hai II | SC-79 and fumonisin B1 |
| 135 | hai II | PDGF and fumonisin B1 |
| 136 | C646 and SGC-CBP30 | SC-79 and PDGF |
| 137 | C646 and 4'-chloro-3-hydroxy-2-naphthanilide | SC-79 and PDGF |
| 138 | C646 and curcumin | SC-79 and PDGF |
| 139 | SGC-CBP30 and 4'-chloro-3-hydroxy-2-naphthanilide | SC-79 and PDGF |
| 140 | 4'-chloro-3-hydroxy-2-naphthanilide and curcumin | SC-79 and PDGF |
| 141 | C646 and PF-CBP1 | SC-79 and PDGF |
| 142 | C646 and hai II | SC-79 and PDGF |
| 143 | SGC-CBP30 and PF-CBP1 | SC-79 and PDGF |
| 144 | SGC-CBP30 and hai II | SC-79 and PDGF |
| 145 | 4'-chloro-3-hydroxy-2-naphthanilide and PF-CBP1 | SC-79 and PDGF |
| 146 | 4'-chloro-3-hydroxy-2-naphthanilide and hai II | SC-79 and PDGF |
| 147 | curcumin and PF-CBP1 | SC-79 and PDGF |
| 148 | curcumin and hai II | SC-79 and PDGF |
| 149 | C646 and SGC-CBP30 | SC-79 and fumonisin B1 |
| 150 | C646 and 4'-chloro-3-hydroxy-2-naphthanilide | SC-79 and fumonisin B1 |
| 151 | C646 and curcumin | SC-79 and fumonisin B1 |
| 152 | SGC-CBP30 and 4'-chloro-3-hydroxy-2-naphthanilide | SC-79 and fumonisin B1 |
| 153 | 4'-chloro-3-hydroxy-2-naphthanilide and curcumin | SC-79 and fumonisin B1 |
| 154 | C646 and PF-CBP1 | SC-79 and fumonisin B1 |
| 155 | C646 and hai II | SC-79 and fumonisin B1 |
| 156 | SGC-CBP30 and PF-CBP1 | SC-79 and fumonisin B1 |
| 157 | SGC-CBP30 and hai II | SC-79 and fumonisin B1 |
| 158 | 4'-chloro-3-hydroxy-2-naphthanilide and PF-CBP1 | SC-79 and fumonisin B1 |
| 159 | 4'-chloro-3-hydroxy-2-naphthanilide and hai II | SC-79 and fumonisin B1 |
| 160 | curcumin and PF-CBP1 | SC-79 and fumonisin B1 |
| 161 | curcumin and hai II | SC-79 and fumonisin B1 |
| 162 | C646 and SGC-CBP30 | PDGF and fumonisin B1 |
| 163 | C646 and 4'-chloro-3-hydroxy-2-naphthanilide | PDGF and fumonisin B1 |
| 164 | C646 and curcumin | PDGF and fumonisin B1 |
| 165 | SGC-CBP30 and 4'-chloro-3-hydroxy-2-naphthanilide | PDGF and fumonisin B1 |
| 166 | 4'-chloro-3-hydroxy-2-naphthanilide and curcumin | PDGF and fumonisin B1 |
| 167 | C646 and PF-CBP1 | PDGF and fumonisin B1 |
| 168 | C646 and hai II | PDGF and fumonisin B1 |
| 169 | SGC-CBP30 and PF-CBP1 | PDGF and fumonisin B1 |
| 170 | SGC-CBP30 and hai II | PDGF and fumonisin B1 |
| 171 | 4'-chloro-3-hydroxy-2-naphthanilide and PF-CBP1 | PDGF and fumonisin B1 |
| 172 | 4'-chloro-3-hydroxy-2-naphthanilide and hai II | PDGF and fumonisin B1 |
| 173 | curcumin and PF-CBP1 | PDGF and fumonisin B1 |
| 174 | curcumin and hai II | PDGF and fumonisin B1 |
| 175 | C646, SGC-CBP30 and 4'-chloro-3-hydroxy-2-naphthanilide | SC-79 and PDGF |
| 176 | C646, SGC-CBP30 and curcumin | SC-79 and PDGF |
| 177 | C646, SGC-CBP30 and PF-CBP1 | SC-79 and PDGF |
| 178 | C646, SGC-CBP30 and hai II | SC-79 and PDGF |
| 179 | SGC-CBP30, 4'-chloro-3-hydroxy-2-naphthanilide and curcumin | SC-79 and PDGF |
| 180 | SGC-CBP30, 4'-chloro-3-hydroxy-2-naphthanilide and PF-CBP1 | SC-79 and PDGF |
| 181 | SGC-CBP30, 4'-chloro-3-hydroxy-2-naphthanilide and hai II | SC-79 and PDGF |
| 182 | C646, PF-CBP1 and hai II | SC-79 and PDGF |
| 183 | SGC-CBP30, PF-CBP1 and hai II | SC-79 and PDGF |
| 184 | 4'-chloro-3-hydroxy-2-naphthanilide, PF-CBP1 and hai II | SC-79 and PDGF |
| 185 | curcumin, PF-CBP1 and hai II | SC-79 and PDGF |
| 186 | C646, SGC-CBP30 and 4'-chloro-3-hydroxy-2-naphthanilide | SC-79 and fumonisin B1 |
| 187 | C646, SGC-CBP30 and curcumin | SC-79 and fumonisin B1 |
| 188 | C646, SGC-CBP30 and PF-CBP1 | SC-79 and fumonisin B1 |
| 189 | C646, SGC-CBP30 and hai II | SC-79 and fumonisin B1 |
| 190 | SGC-CBP30, 4'-chloro-3-hydroxy-2-naphthanilide and curcumin | SC-79 and fumonisin B1 |
| 191 | SGC-CBP30, 4'-chloro-3-hydroxy-2-naphthanilide and PF-CBP1 | SC-79 and fumonisin B1 |
| 192 | SGC-CBP30, 4'-chloro-3-hydroxy-2-naphthanilide and hai II | SC-79 and fumonisin B1 |
| 193 | C646, PF-CBP1 and hai II | SC-79 and fumonisin B1 |
| 194 | SGC-CBP30, PF-CBP1 and hai II | SC-79 and fumonisin B1 |

TABLE 1-continued

Combinations of CREB inhibitors and Akt activators that can be used for favoring wound healing

| Combination | CREB inhibitor(s) | Akt activator(s) |
| --- | --- | --- |
| 195 | 4'-chloro-3-hydroxy-2-naphthanilide, PF-CBP1 and hai II | SC-79 and fumonisin B1 |
| 196 | curcumin, PF-CBP1 and hai II | SC-79 and fumonisin B1 |
| 197 | C646, SGC-CBP30 and 4'-chloro-3-hydroxy-2-naphthanilide | PDGF and fumonisin B1 |
| 198 | C646, SGC-CBP30 and curcumin | PDGF and fumonisin B1 |
| 199 | C646, SGC-CBP30 and PF-CBP1 | PDGF and fumonisin B1 |
| 200 | C646, SGC-CBP30 and hai II | PDGF and fumonisin B1 |
| 201 | SGC-CBP30, 4'-chloro-3-hydroxy-2-naphthanilide and curcumin | PDGF and fumonisin B1 |
| 202 | SGC-CBP30, 4'-chloro-3-hydroxy-2-naphthanilide and PF-CBP1 | PDGF and fumonisin B1 |
| 203 | SGC-CBP30, 4'-chloro-3-hydroxy-2-naphthanilide and hai II | PDGF and fumonisin B1 |
| 204 | C646, PF-CBP1 and hai II | PDGF and fumonisin B1 |
| 205 | SGC-CBP30, PF-CBP1 and hai II | PDGF and fumonisin B1 |
| 206 | 4'-chloro-3-hydroxy-2-naphthanilide, PF-CBP1 and hai II | PDGF and fumonisin B1 |
| 207 | curcumin, PF-CBP1 and hai II | PDGF and fumonisin B1 |
| 208 | C646 | SC-79, PDGF and fumonisin B1 |
| 209 | SGC-CBP30 | SC-79, PDGF and fumonisin B1 |
| 210 | 4'-chloro-3-hydroxy-2-naphthanilide | SC-79, PDGF and fumonisin B1 |
| 211 | curcumin | SC-79, PDGF and fumonisin B1 |
| 212 | PF-CBP1 | SC-79, PDGF and fumonisin B1 |
| 213 | hai II | SC-79, PDGF and fumonisin B1 |
| 214 | C646 and SGC-CBP30 | SC-79, PDGF and fumonisin B1 |
| 215 | C646 and 4'-chloro-3-hydroxy-2-naphthanilide | SC-79, PDGF and fumonisin B1 |
| 216 | C646 and curcumin | SC-79, PDGF and fumonisin B1 |
| 217 | SGC-CBP30 and 4'-chloro-3-hydroxy-2-naphthanilide | SC-79, PDGF and fumonisin B1 |
| 218 | 4'-chloro-3-hydroxy-2-naphthanilide and curcumin | SC-79, PDGF and fumonisin B1 |
| 219 | C646 and PF-CBP1 | SC-79, PDGF and fumonisin B1 |
| 220 | C646 and hai II | SC-79, PDGF and fumonisin B1 |
| 221 | SGC-CBP30 and PF-CBP1 | SC-79, PDGF and fumonisin B1 |
| 222 | SGC-CBP30 and hai II | SC-79, PDGF and fumonisin B1 |
| 223 | 4'-chloro-3-hydroxy-2-naphthanilide and PF-CBP1 | SC-79, PDGF and fumonisin B1 |
| 224 | 4'-chloro-3-hydroxy-2-naphthanilide and hai II | SC-79, PDGF and fumonisin B1 |
| 225 | curcumin and PF-CBP1 | SC-79, PDGF and fumonisin B1 |
| 226 | curcumin and hai II | SC-79, PDGF and fumonisin B1 |
| 227 | C646 and SGC-CBP30 | SC-79, PDGF and fumonisin B1 |
| 228 | C646 and 4'-chloro-3-hydroxy-2-naphthanilide | SC-79, PDGF and fumonisin B1 |
| 229 | C646 and curcumin | SC-79, PDGF and fumonisin B1 |
| 230 | SGC-CBP30 and 4'-chloro-3-hydroxy-2-naphthanilide | SC-79, PDGF and fumonisin B1 |
| 231 | 4'-chloro-3-hydroxy-2-naphthanilide and curcumin | SC-79, PDGF and fumonisin B1 |
| 232 | C646 and PF-CBP1 | SC-79, PDGF and fumonisin B1 |
| 233 | C646 and hai II | SC-79, PDGF and fumonisin B1 |
| 234 | SGC-CBP30 and PF-CBP1 | SC-79, PDGF and fumonisin B1 |
| 235 | SGC-CBP30 and hai II | SC-79, PDGF and fumonisin B1 |
| 236 | 4'-chloro-3-hydroxy-2-naphthanilide and PF-CBP1 | SC-79, PDGF and fumonisin B1 |
| 237 | 4'-chloro-3-hydroxy-2-naphthanilide and hai II | SC-79, PDGF and fumonisin B1 |
| 238 | curcumin and PF-CBP1 | SC-79, PDGF and fumonisin B1 |
| 239 | curcumin and hai II | SC-79, PDGF and fumonisin B1 |
| 240 | C646, SGC-CBP30 and 4'-chloro-3-hydroxy-2-naphthanilide | SC-79, PDGF and fumonisin B1 |
| 241 | C646, SGC-CBP30 and curcumin | SC-79, PDGF and fumonisin B1 |
| 242 | C646, SGC-CBP30 and PF-CBP1 | SC-79, PDGF and fumonisin B1 |
| 243 | C646, SGC-CBP30 and hai II | SC-79, PDGF and fumonisin B1 |
| 244 | SGC-CBP30, 4'-chloro-3-hydroxy-2-naphthanilide and curcumin | SC-79, PDGF and fumonisin B1 |
| 245 | SGC-CBP30, 4'-chloro-3-hydroxy-2-naphthanilide and PF-CBP1 | SC-79, PDGF and fumonisin B1 |
| 246 | SGC-CBP30, 4'-chloro-3-hydroxy-2-naphthanilide and hai II | SC-79, PDGF and fumonisin B1 |
| 247 | C646, PF-CBP1 and hai II | SC-79, PDGF and fumonisin B1 |
| 248 | SGC-CBP30, PF-CBP1 and hai II | SC-79, PDGF and fumonisin B1 |
| 249 | 4'-chloro-3-hydroxy-2-naphthanilide, PF-CBP1 and hai II | SC-79, PDGF and fumonisin B1 |
| 250 | curcumin, PF-CBP1 and hai II | SC-79, PDGF and fumonisin B1 |
| 251 | C646, SGC-CBP30 and 4'-chloro-3-hydroxy-2-naphthanilide | SC-79, PDGF and fumonisin B1 |
| 252 | C646, SGC-CBP30 and curcumin | SC-79, PDGF and fumonisin B1 |
| 253 | C646, SGC-CBP30 and PF-CBP1 | SC-79, PDGF and fumonisin B1 |
| 254 | C646, SGC-CBP30 and hai II | SC-79, PDGF and fumonisin B1 |

TABLE 1-continued

Combinations of CREB inhibitors and Akt activators that can be used for favoring wound healing

| Combination | CREB inhibitor(s) | Akt activator(s) |
|---|---|---|
| 255 | SGC-CBP30, 4'-chloro-3-hydroxy-2-naphthanilide and curcumin | SC-79, PDGF and fumonisin B1 |
| 256 | SGC-CBP30, 4'-chloro-3-hydroxy-2-naphthanilide and PF-CBP1 | SC-79, PDGF and fumonisin B1 |
| 257 | SGC-CBP30, 4'-chloro-3-hydroxy-2-naphthanilide and hai II | SC-79, PDGF and fumonisin B1 |
| 258 | C646, PF-CBP1 and hai II | SC-79, PDGF and fumonisin B1 |
| 259 | SGC-CBP30, PF-CBP1 and hai II | SC-79, PDGF and fumonisin B1 |
| 260 | 4'-chloro-3-hydroxy-2-naphthanilide, PF-CBP1 and hai II | SC-79, PDGF and fumonisin B1 |
| 261 | curcumin, PF-CBP1 and hai II | SC-79, PDGF and fumonisin B1 |

In the context of the present disclosure, the CREB inhibitor(s) and the Akt activator(s) can be administered simultaneously or in an alternate fashion. The specific combinations described herein can be used alone or in combination with another therapeutic agent known to favor wound healing. Such additional therapeutic agents include, without limitations, growth hormones and antibiotics.

The compounds and combinations described herein can be used prophylactically for preventing pathological wound healing. For example, the compounds and combinations described herein can be used prior to surgery to the eye (especially of the cornea) or to the skin.

The compounds and combinations described herein can also be used therapeutically for favoring wound healing by accelerating wound closure. For example, the compounds and combinations described herein can be used on an epithelial wound.

The compounds and combinations described herein can also be used prophylactically and therapeutically prior to the onset of the wound as well as once the wound has been made to the epithelium.

The compounds and combinations can be delivered through any route such as, intravenous, cutaneous, intra-arterial, parenteral, subcutaneous, intramuscular, intracranial, intra-orbital, ophthalmic, intraventricular, intracapsular, intraspinal, intrathecal, epidural, intracisternal, intraperitoneal, oral and intranasal. In some embodiments, the compounds and combinations are formulated for administration directly to the wound or to the vicinity of the wound. As such, some of the compounds and combinations described herein can be used for topical administration to a damaged epithelium, such as the cornea or the skin.

The compounds and combinations described herein can be formulated in the form of ointments, drops (eye or nasal), creams, tablets, pills, capsules, suppositories, powders, enterically coated or other protected formulations, sustained release formulations, solutions, suspensions, elixirs, aerosols, and the like.

In an embodiment, the compounds and compositions are placed in direct contact with the epithelial wound. The compounds and compositions can be applied topically (or formulated for topical administration) to the wound or in the vicinity of the wound. The compounds and compositions can also be applied topically (or formulated for topical administration) to the wound and in the vicinity of the wound. In embodiments in which the compounds and compositions are to be applied to the cornea, the compounds and compositions can be formulated as an eye drop or an ophthalmologic ointment. In embodiments in which the compounds and the compositions are to be applied to the skin, the compounds and compositions can be formulated as an aerosol, a cream or an ointment.

The compounds and combinations described herein can be formulated as pharmaceutical composition in combination with a pharmaceutically-acceptable carrier. In the present disclosure, a "carrier", a "pharmaceutical carrier" or a "pharmaceutically-acceptable carrier" is a pharmaceutically acceptable solvent, suspending agent or any other pharmacologically inert vehicle for delivering one or more active compounds to the subject. The carrier is typically a liquid or a solid. When the compounds and combinations are intended to be delivered directly to the eye, the carrier must also be considered acceptable for ophthalmologic applications. A pharmaceutical carrier is generally selected to provide for the desired bulk, consistency, etc., when combined with components of a given pharmaceutical composition, in view of the intended administration mode. Typical pharmaceutical carriers include, but are not limited to binding agents; fillers; lubricants; disintegrants and wetting agents.

In embodiments in which the compounds and combinations are intended to be administered to favor the healing of a wound located in an eye (for example a corneal wound), it is possible to use muco-adhesive gold nanoparticles to deliver the compounds or the combinations to the eye (especially to the cornea). Exemplary gold nanoparticles are described in Boisselier et al., 2008.

The compounds and combinations can be formulated in the presence of additional pharmaceutical excipients including starch, cellulose, talc, glucose, lactose, gelatin, malt, rice, flour, chalk, silica, magnesium stearate, sodium stearate, glycerol monostearate, sodium chloride, dried skim milk, glycerol, propylene glycol, water, ethanol, and the like. The compounds and combinations may be subjected to conventional pharmaceutical additives such as preservatives, stabilizing agents, wetting or emulsifying agents, salts for adjusting osmotic pressure, buffers and the like.

In addition, the compounds and combinations herein described are administered at a "pharmaceutically effective amount", "therapeutically effective amount" or "wound healing sufficient amount". Collectively, these terms refer to an amount (dose) effective in favoring wound healing. It is also to be understood herein that a "pharmaceutically effective amount", "therapeutically effective amount" or "wound healing sufficient amount" may be interpreted as an amount giving a desired therapeutic effect, either taken in one dose or in any dosage or route, taken alone or in combination with other therapeutic agents.

The present disclosure also provides screening assays for identifying additional compounds or combinations that can favor wound healing. As shown herein, the present disclosure indicates that by activating the AKT signaling pathway (in some embodiments by activating Akt) and/or inhibiting the MAPK signaling pathway (in some embodiments by inhibiting CREB), it is possible to favor wound healing by accelerating wound closure. Therefore, the screening assays of the present disclosure are based on a tested agent's (or a combination of tested agents) ability to activate the AKT signaling pathway and/or to inhibit the MAPK signaling to determine its usefulness in favoring wound healing.

More specifically, in the screening assays of the present disclosure, a test compound or a combination of test compounds are contacted with a first epithelial cell or a plurality of first epithelial cells. The epithelial cell can be in or derived from any epithelium. In some embodiments, the epithelial cell can be corneal epithelial cells. In another embodiment, the epithelial cells can be skin keratinocytes. In further embodiments, the epithelial cell can be located in an in vitro model. The in vitro model can be, for example a skin in vitro model or a cornea in vitro model, such as, for example, the in vitro cornea model described in Carrier et al. 2008 or in the Example of the present disclosure. The in vitro skin model can comprise cultured fibroblasts, cultured skin epithelial cells and an extracellular matrix substantially produced by the cultured cells. The in vitro cornea model can comprise cultured keratocytes, cultured epithelial corneal cells and an extracellular matrix substantially produced by the cultured keratocytes and the cultured epithelial corneal cells. In some embodiments, it is possible to use an in vitro skin or cornea model which has been wounded to screen for the test compound or the combination of test compounds.

Once the test compound or the combination of test compounds has been contacted with the first epithelial cell(s), it is then determined if the test compound, or the combination of test compounds, have the ability to activate the AKT pathway (and, in some embodiments, activate Akt itself) and/or inhibit the MAPK pathway (and, in some embodiments, inhibit CREB). This can be done by comparing the status of the AKT and/or MAPK pathways in a cell which has not been in contact with the test compound or the combination of test compounds (for example, the first epithelial cell prior to the contacting step) or a cell which has been in contact with a control compound (such as, for example DMSO) or a combination of control compounds known not to activate the AKT pathway and/or inhibit the MAPK pathway. The determination step can also be achieved by determining the phosphorylation status of the members of the AKT and/or the MAPK pathways. For example, a test compound or a combination of test compounds capable of causing or increasing the phosphorylation status of Akt is determined to activate Akt and the AKT pathway. In yet another example, a test compound or a combination of test compounds capable of decreasing or dephosphorylating CREB is determined to inhibit CREB and the MAPK pathway. This can also be achieved by determining the rate of wound closure, when a "wounded" skin, an in vitro skin model or corneal in vitro model is used.

Once the determination has been made, the compound or the combination of compounds can be characterized. If the test compound or the combination of test compounds is determined to activate the AKT pathway, it is considered to be useful for favoring wound healing. If the test compounds or the combination of test compounds is determined to inhibit the MAPK pathway, it is considered to be useful for favoring wound healing. If the test compound or the combination of test compounds is determined to activate the AKT pathway and to inhibit the MAPK pathway, it is considered to be useful for favoring wound healing.

The present disclosure further provides a model of a cornea for studying in vitro the wound healing process. The in vitro cornea model comprises at least one stromal tissue sheet on which corneal epithelial cells are seeded and cultured. The in vitro cornea model has two distinct regions: a stromal region (composed of cultured corneal fibroblasts and the extracellular matrix the cultured corneal fibroblasts have made and assembled) and an epithelium (composed of cultured corneal epithelial cells). The epithelium is preferably a differentiated epithelium. The in vitro cornea model also has, at least in some regions of the model, a basal membrane connecting the epithelial cells to the stromal region. The cells used to prepare the in vitro cornea model can be derived from human cells. In an embodiment, the in vitro cornea model is a human in vitro cornea model because the cells of the model are human cells and the extracellular matrix of the model is made from the cultured human cells.

The corneal stromal tissue sheet comprises cultured corneal fibroblasts (also referred to as keratocytes) and the extracellular matrix such cultured corneal fibroblasts secrete and assemble when cultured in the presence of ascorbic acid. The corneal stromal tissue sheet is substantially devoid of exogenous extracellular matrix (ECM) components, e.g. ECM components which have not been produced or assembled by the cultured cells. The in vitro corneal model comprises at least one stromal tissue sheet. In some embodiments, the in vitro corneal model comprises at least two, three, four, five or more stromal tissue sheets which have been stacked and fused together during culture. In an embodiment, the in vitro corneal model comprises two stromal tissue sheets which have been stacked and fused together during culture.

Once the stromal region (obtained by providing a single stromal tissue sheet or staking and fusing a plurality of stromal tissue sheets) has been obtained, epithelial cells are seed on one of the faces of the stromal region ("air face"), while the other face is not seed with epithelial cells ("liquid face"). Then, the in vitro model is brought to the air-liquid interface to allow the differentiation of the epithelial cells. In the context of the present disclosure, "bringing to the air-liquid interface" refers to a step of placing the model at the air-liquid interface of a liquid culture medium, wherein its "air" face is in contact with air and its "liquid" face is in contact with the liquid culture medium.

The in vitro model comprises cultured corneal fibroblasts, cultured corneal epithelial cells as well as the extracellular matrix which has at least been partially produced and assembled by the cultured cells. In an embodiment, the in vitro cornea model is substantially devoided of exogenous extracellular matrix (ECM) components, e.g. ECM components which have not been produced or assembled by the cultured cells. In still another embodiment, the extracellular matrix of the in vitro cornea model is exclusively produced by the cultured cells. The in vitro cornea model can comprise cells of any origin. The in vitro cornea model can comprise cells and/or extracellular matrix components of human origin.

In order to study the healing of a wound, a wound can be made to the in vitro cornea model. The wound can be made anywhere on the in vitro cornea, and preferably at the center of the in vitro cornea. The wound can be made using any mechanical or chemical means, and preferably by using a biopsy punch.

In some embodiments, to allow the re-epithelialization of the wounded in vitro cornea, the "liquid" face of the cornea is placed in contact with at least one (and in some embodiments a plurality of) stromal tissue sheet. Without wishing to be bound to theory, the presence of a further stromal sheet allows the epithelial cells at the wound margin to migrate and close the in vitro wound.

The present invention will be more readily understood by referring to the following examples which are given to illustrate the invention rather than to limit its scope.

EXAMPLE I

In Vitro Cornea Model for Studying Wound Healing

Cell Culture and Production of the Tissue-Engineered Human Corneas. Human corneal epithelial cells (HCECs) were isolated from the limbal area of normal eyes of 44-, 52- and 71 year-old donors following a procedure previously described; the eyes were obtained from the Banque d'Yeux Nationale of the Centre Universitaire d'Ophtalmologie (CHU de Québec, Hôpital du Saint-Sacrement, Québec, QC, Canada). HCECs were primary cultured with a feeder layer of irradiated murine Swiss-3T3 fibroblasts (ATCC, Rockville, Md.). Human corneal fibroblasts were isolated from the stromal portion of a cornea (from a 26 days-old donor) left after dispase digestion and removal of both the endothelium and epithelium, and primary cultured and subcultured. All cells were grown under 8% $CO_2$ at 37° C. and culture medium was changed after 2-3 days.

Figure 2A:
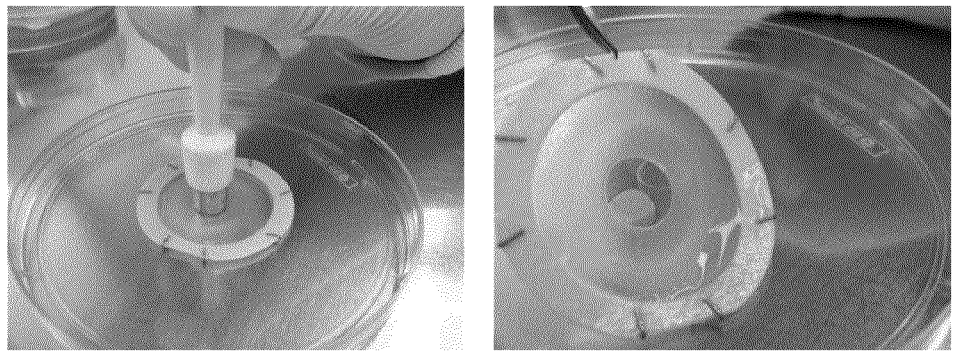
FIGS. 2A to D illustrate the production of wounds on tissue-engineered human corneas. (A) The reconstructed cornea is wounded using a 8-mm biopsy punch. (B) Schematic representation of the areas from the wounded reconstructed corneas that were recovered to prepare total RNA for the microarray analysis. (C) Closure of wounds on tissue-engineered corneas produced using human corneal epithelial cells isolated from the eyes of three different donors (of 44-, 52- and 71 years old). Closure of the wounded epithelia has been followed from 1 to 4 days after corneal injury. (D) Composite image showing a complete view of the wounded, tissue engineered human cornea 3 days following corneal damage (sections were stained with Masson trichrome; cells are pink and collagen is bluish).

The tissue-engineered, two-layers 3D human corneas that have been used as a biomaterial were produced following the self-assembly approach (see FIG. 1). Briefly, corneal fibroblasts were seeded and cultured in fibroblast growth medium supplemented with 50 μg/ml ascorbic acid (Sigma, Oakville, Ont., Canada) for 35 days. Ascorbic acid allows fibroblasts to secrete and lay down their own ECM. After peeling from the flasks, two tissue sheets were superimposed to form a reconstructed stroma and were cultured for another week so that they could adhere to each other. Then, human corneal epithelial cells (HCECs) isolated from donors of different ages (44-, 52- and 71-years old) were seeded on the surface of the reconstructed stroma and cultured in submerged conditions in complete epithelial cell medium supplemented with ascorbate, as previously described (Carrier et al., 2008). After 7 days, reconstructed tissues were fed an EGF-free epithelial cell medium and were raised at the air-liquid interface for 10 days to induce epithelial differentiation. Reconstructed partial thickness corneas produced by the self-assembly approach were then wounded using a biopsy punch. After wounding, the tissue-engineered corneas were placed over two supplementary fibroblast sheets to allow reepithelialization over a natural matrix. Wound closure was then examined macroscopically every 24 hours for 4 days following the initial damage by observing the ring of reepithelialization that progressed toward the wound center. Biopsy samples were photographed at regular intervals (24 hours) using a Zeiss Imager.Z2 microscope (Zeiss Canada Ltd, North York, ON, Canada) equipped with a numeric CCD camera (AxioCam MRm; Zeiss). All experiments were repeated four times. When indicated, corneal stromas were depleted of their corneal fibroblasts by a 3 min treatment with 0.5% sodium deoxycholate followed by five washes with 1×PBS. Macroscopic views of the wounded reconstructed stroma are shown at FIG. 2A.

Mass Spectrometry. The digest and mass spectrometry experiments were performed by the Proteomics platform of the Eastern Quebec Genomics Center, CHU de Quebec, Canada. Punch biopsies (8 mm diameter) taken either from complete tissue-engineered corneas (stroma/HCEC+) or just the stromal matrix without epithelial cells (stroma/HCEC−) were first dissolved in ammonium bicarbonate 50 mM (10 μl), reduced and alkylated with DTT 45 mM and Iodoacetamide 100 mM, then digested with 126 nM of modified porcine trypsin (Sequencing grade, Promega, Madison, Wis.) at 58° C. for 1 h. Digestion products were extracted using 1% formic acid, 2% acetonitrile followed by 1% formic acid, 50% acetonitrile. The recovered extracts were pooled, vacuum centrifuge dried, desalted and then resuspended into 10 μl of 0.1% formic acid and 2 μl were analyzed by mass spectrometry. Peptide samples were separated by online reversed-phase (RP) nanoscale capillary liquid chromatography and analyzed by electrospray mass spectrometry (ES MS/MS). The experiments were performed with a Thermo Surveyor MS pump connected to a LTQ linear ion trap mass spectrometer equipped with a nanoelectrospray ion source (Thermo Fisher Scoentific Inc., San Jose, Calif. USA). Peptide separation took place on a self-packed PicoFrit column (New Objective, Woburn, Mass.) packed with Jupiter (Phenomenex) 5μ, 300A C18, 10 cm×0.075 mm internal diameter. Peptides were eluted with a linear gradient from 2-50% solvent B (acetonitrile, 0.1% formic acid) in 30 minutes, at 200 nL/min (obtained by flow-splitting). Mass spectra were acquired using a data dependent acquisition mode with Xcalibur software version 2.0. Each full scan mass spectrum (400 to 2000 m/z) was followed by collision-induced dissociation of the seven most intense ions. The dynamic exclusion (30 sec exclusion duration) function was enabled, and the relative collisional fragmentation energy was set to 35%. All MS/MS samples were analyzed using Mascot (Matrix Science, London, UK; version 2.3.0)). Mascot was searched with a fragment ion mass tolerance of 0.50 Da and a parent ion tolerance of 2.0 Da. Iodoacetamide derivative of cysteine was specified as a fixed modification and oxidation of methionine was specified as a variable modification. Two missed cleavages were allowed. Scaffold (version 4) (Proteome Software Inc., Portland, Oreg.) was used to validate MS/MS based peptide and protein identifications. Peptide identifications were accepted if they could be established at greater than 95% probability as specified by the Peptide Prophet algorithm. Protein probabilities were assigned by the Protein Prophet algorithm.

Western Blots. Protein extracts for Western blot analyses were concentrated from culture media using a Centricon Ultracel YM-10 column (EMD Millipore, Darmstadt, Germany). Western blots were conducted using the following primary antibodies: a mouse polyclonal antibody against MMP1 (1:5000; Thermo Fisher Scientific Inc., Rockford, Ill., USA) or rabbit polyclonal antibodies against MMP2 (1:10000; Thermo Fisher Scientific Inc.), MMP3 (1:3000; Thermo Fisher Scientific Inc.), MMP9 (1:1000; Abcam, Toronto, ON, Canada), MMP10 (1:3000; Thermo Fisher Scientific Inc.), MMP11 (1:5000; Thermo Fisher Scientific Inc.), MMP13 (1:5000; Thermo Fisher Scientific Inc.), Sp1 (1:2000; Santa Cruz Biotechnology, Dallas, Tex., USA), c-Fos (1:2000; Santa Cruz), c-Jun (1:2000; Santa Cruz), JunB (1:2000; Santa Cruz) and actin (1:40000; Santa Cruz) as well as a peroxidase-conjugated AffiniPure Goat secondary antibody against either mouse or rabbit IgG (1:1000 dilution; Jackson ImmunoResearch Laboratories, Baltimore, Pa., USA). The labeling was revealed using a Detection Kit (Amersham, Baie d'Urfé, Canada). Whenever possible, expression of both the inactive (pro-enzyme) and active MMPs was examined throughout wound closure (which depended on whether antibodies could detect both the active and inactive MMPs or just the inactive one).

Figure 2B:
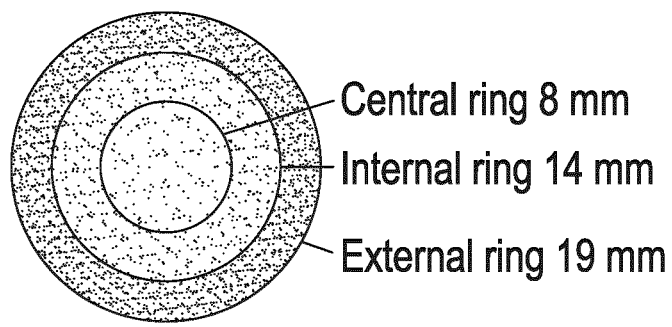

Gene Expression Profiling. The epithelial cells from biopsy punch-wounded tissue-engineered corneas were isolated from three different areas after 4-days of culture at the air-liquid interface: i) a central area of 8 mm in diameter (wounded) that contains the neoepithelium, ii) the internal (unwounded) ring, that includes tissue surrounding the wounded central area and contained between diameter 8 to 14 mm of the tissue-engineered cornea, and iii) the external ring, an area that surrounds the unwounded internal ring from diameter 14 to 19 mm (see FIG. 2B). As negative controls, cells were also isolated from the same three areas of unwounded tissue-engineered corneas. Total RNA was then prepared from the material isolated from the central, internal or external rings using the RNeasy Mini Kit (QIAGEN, Toronto, ON, CA). It is important to point out that because corneal fibroblasts are less abundant (36.2+/−1.0%) than epithelial cells (63.9+/−0.9%) are in the reconstructed tissue, and that they are trapped in the stromal collagen matrix and not mitotically active, they will not significantly contribute to the total RNAs isolated as nearly all of it will originate from the epithelial cells. RNAs were also isolated from HCECs grown to 100% confluence on 2% BSA, on individual ECM components (collagens type I (CI) and IV (CIV), FN, tenascin (TN) and laminin (LM)) or on tissue-reconstructed stromas depleted (by treating them with 0.5 deoxycholate; stroma−) or not (stroma+) of their corneal fibroblasts. Quantity and quality of all preparation of total RNA was assessed using an Agilent Technologies 2100 bioanalyzer and RNA 6000 Nano LabChip kit (Agilent Technologies, Mississauga, ON, Canada). Biological replicates were as follow: for the wound healing experiment conducted on the tissue-engineered corneas made-up of a stroma with a complete, stratified epithelium, total RNA was obtained from 3 different reconstructed corneas produced using HCECs cultured from 3 different donors (44-, 52- and 71-year old); for the monolayer experiment on BSA, total RNA was obtained from 5 different preparations of HCECs cultured from 3 different donors (44-, 52- and 71-year old); for the stroma− condition, total RNA was isolated from 3 preparations of HCECs cultured from 3 different donors (44-, 52- and 71-year old); for the stroma+ condition, total RNA was isolated from 2 preparations of HCECs cultured from 2 different donors (44- and 52-year old). For the monolayer experiments on CI, CIV, LM, FN and TN, total RNA was obtained from 5 different preparations of HCECs cultured from 3 different donors (44-, 52- and 71-year old). Cyanine 3-CTP labeled cRNA targets were prepared from 50 ng of total RNA, using the Agilent One-Color Microarray-Based Gene Expression Analysis kit (Agilent Technologies). Then, 600 ng cRNA was incubated on a G4851A SurePrint G3 Human GE 8x60K array slide (60 000 probes, Agilent Technologies). Slides were then hybridized (Agilent protocol), washed and scanned on an Agilent SureScan Scanner according to the manufacturer's instructions. Data were finally analyzed using the ArrayStar V12 (DNASTAR, Madison, Wis., USA) software for scatter plots and generation of the heat maps of selected genes of interest. All data generated from the arrays were also analyzed by RMA ('Robust Multiarray Analysis') for background correction of the raw values. They were then transformed in Log 2 base and robust multiarray analysis (RMA) quantile normalized before a linear model was fitted to the normalized data to obtain an expression measure for each probe set on each array. All microarray data presented in this study comply with the Minimum Information About a Microarray Experiment (MIAME) requirements. The gene expression data have been deposited in NCB's Gene Expression Omnibus (GEO, http://www.ncbi.nlm.nih.gov/geo/) and are accessible through GEO Series accession number.

Gelatin Zymography. The zymographic analyses were conducted using samples from the culture media of confluent HCECs that have been grown either on BSA or on various individual ECM components (CI and CIV, FN, TN and LM). MMP2 and MMP9 activity was also monitored in the culture medium of wounded tissue engineered human corneas. Medium samples were harvested at the moment the two-layers corneas were wounded (day 0) and then sequentially at every 24 hours until 4 days of wound closure (days 1 to 4). Reconstructed corneas were changed cultured medium every 24 hours (and also 24 h prior to wounding) to prevent enzyme accumulation.

Quantitative PCR (qPCR). Some of the total RNAs prepared for microarray analyses were also used for qPCR analyses. Reverse transcription was performed using random hexamer primers following the manufacturer's protocol for synthesis of the first strand cDNA (High Capacity cDNA Reverse Transcription Kit; Applied Biosystem, Foster City, Calif., USA). Equal amounts of cDNA were run in quadruplicate and amplified in a 20 µl reaction containing 10 µl of 2× Brillant III Ultra-Fast SYBR Green QPCR Master Mix (Agilent Technologies), 100 nM of upstream and downstream primers, and 1 ng of cDNA target. No-template controls were also used as recommended. The mixture was incubated at 95° C. for 3 min, and then cycled at 95° C. for 10 sec and at 60° C. for 20 sec 35 times using the QIAGEN Rotor-Gene Q real-time cycler. Amplification efficiencies were validated and normalized either to the actin or GAPDH mRNA transcript (as specified in the figure's legends) and quantity of target genes were calculated according to a standard curve. Primers were designed using Primer3 (v.0.4.0) and are listed in Table 2.

Figure 5A:
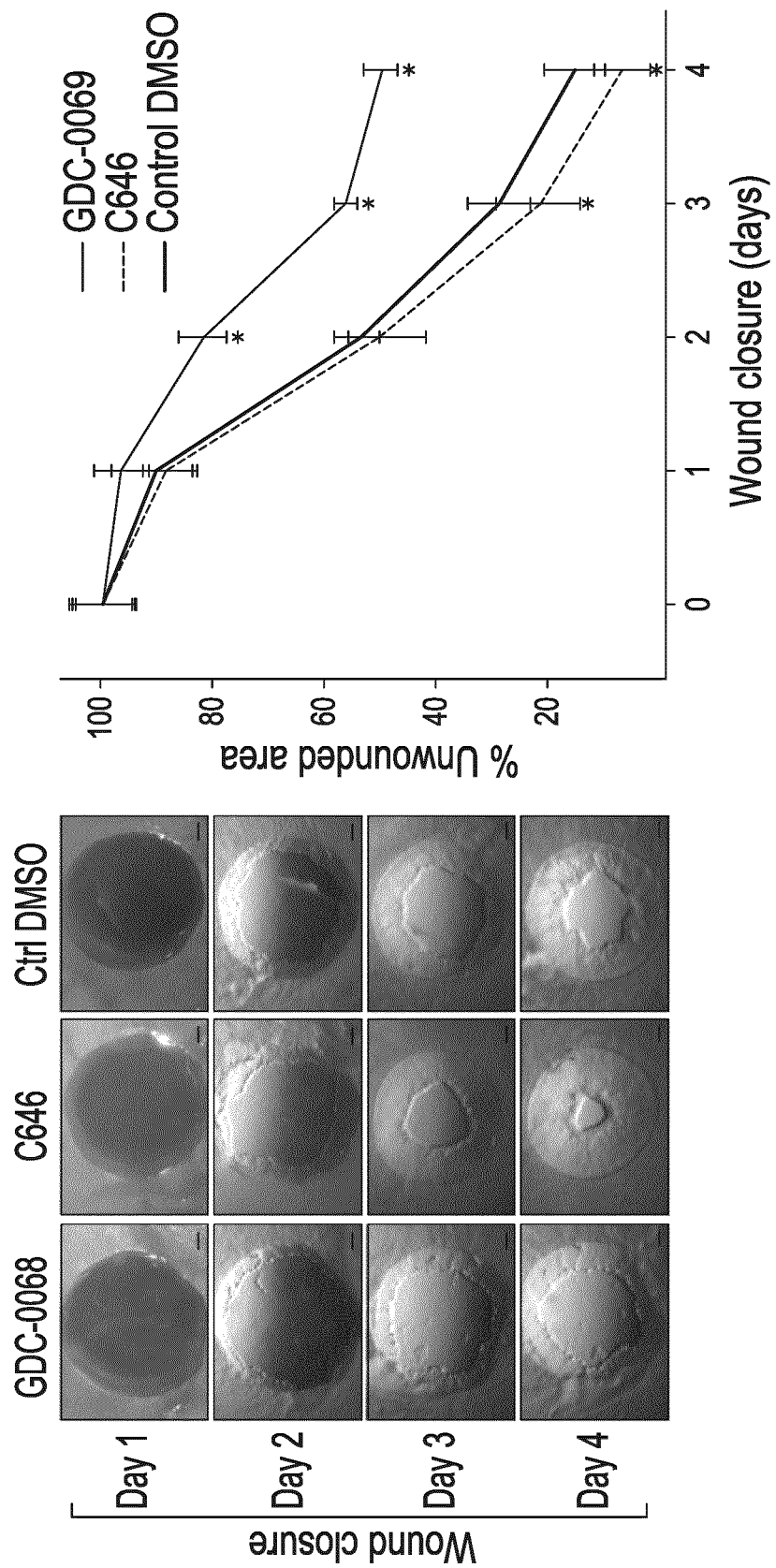
FIGS. 5A to 5C illustrate the pharmacological alteration of Akt and CREB on wound closure dynamic. (A) Left panel: Tissue-engineered human corneas (TEC) (four reconstructed corneas per condition) were wounded as in FIG. 2 and then maintained in culture medium supplemented with GDC-0069 (36 nM, thin line), a pharmacological inhibitor of Akt phosphorylation, and C646 (800 nM, broken line), an inhibitor of CREB phosphorylation. Wounded corneas used as controls were exposed solely to the vehicle (DMSO, thick line). Wound closure was monitored over a 4-day period. Right panel: Measurement of wound surface remaining at each day using the ImageJ64 software (n=4). (B) Left panel: TECs were wounded as in (A) and maintained in culture medium containing C646 (800 nM) along with the AKT agonist SC79 (10 µM) (thin line) or DMSO (broken line). Wound closure was monitored as in (A). Right panel: Measurement of wound surface remaining at each day using the ImageJ64 software (n=4). (C) Composite image showing a complete view of the wounded TECs exposed either to the vehicle (DMSO) or pharmacological compounds (C646, GDC0068 or the combination of C646 and SC79) 4 days following corneal damage (sections were stained with Masson's trichrome; cells are pink and collagen is bluish). The wound margin created by the biopsy punch is indicated.
Figure 5B:
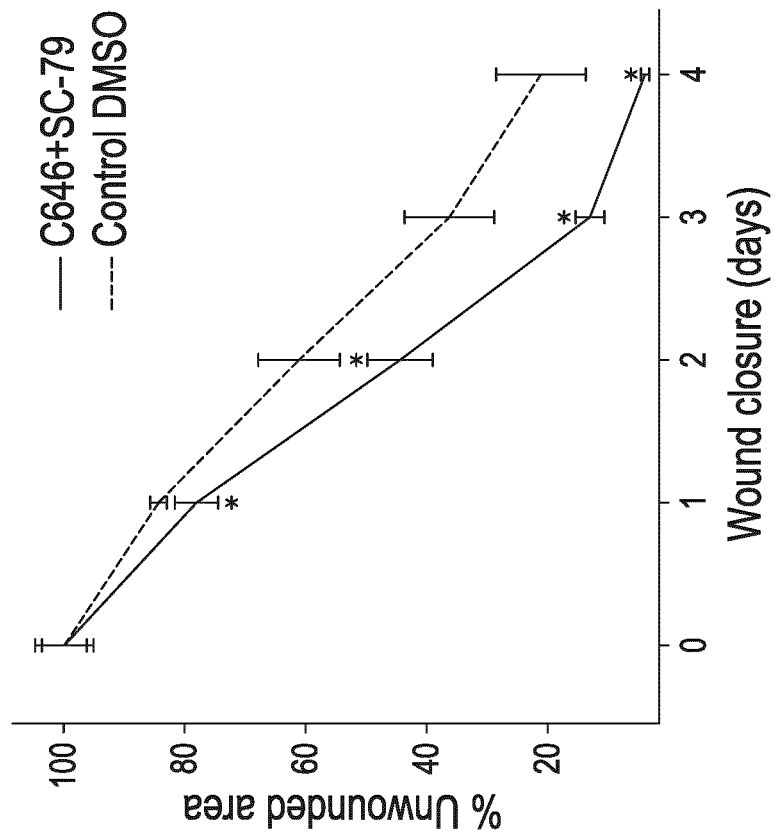
Figure 5B:
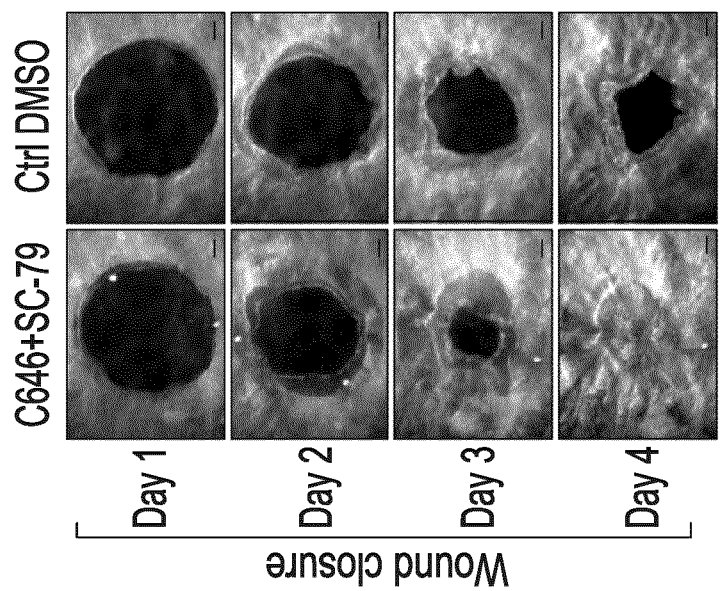

Statistical Analyses. One-way ANOVA or Student's t-test (FIGS. 5A and 5B) were performed for comparison of the groups in qPCR analyses (Prism 6.0; GraphPad Software, La Jolla, Calif.). Differences were considered to be statistically significant at $P<0.05$. All data are also expressed as mean±SD.

TABLE 2

DNA sequence of the primers for qPCR analyses

| Gene | Forward Primer (5'-3')<br>Reverse Primer (5'-3') | SEQ ID NO: | Genebank # |
| --- | --- | --- | --- |
| MMP1 | GGGGCTTTGATGTACCCTAGC<br>TGTCACACGCTTTTGGGGTTT | 1<br>2 | NM_002421 |
| MMP2 | TAGCAGAGCCTAGACAAGGG<br>CAGGACAGAGGGACTAGAGC | 3<br>4 | NM_004530 |
| MMP3 | GTCACTTGTCTGTTGCACACG<br>AGGGAACTTGAGCGTGAATCT | 5<br>6 | NM_002422 |
| MMP9 | GACGGGTATCCCTTCGAC<br>CCGAGTTGGAACCACGAC | 7<br>8 | NM_004994 |
| MMP10 | GCTCTGCCTATCCTCTGAG<br>CACATCCTTTTCGAGGTTG | 9<br>10 | NM_002425 |
| MMP11 | CCGCAACCGACAGAAGAGG<br>ATCGCTCCATACCCTTAGGGC | 11<br>12 | NM_005940 |
| MMP13 | CCAGACTTCACGATGGCATTG<br>CCGCAACCGACAGAAGAGG | 13<br>14 | NM_002427 |

TABLE 2-continued

DNA sequence of the primers for qPCR analyses

| Gene | Forward Primer (5'-3')<br>Reverse Primer (5'-3') | SEQ ID NO: | Genebank # |
|---|---|---|---|
| SP1 | GTCCCTAAGTAAGTTTCTTCC<br>GGAGGCTACAGACTAC | 15<br>16 | NM_003109 |
| FOS | GCTGGTGCATTACAGAGAGG<br>CTCCGGAAGAGGTAAGGAC | 17<br>18 | NM_005252 |
| JUN | GGGCATGTGCTGTGACC<br>CATAAGCAAAGGCCATC | 19<br>20 | NM_002228 |
| ACTB | CAAGATGAGATTGGCATGG<br>GGCCACATTGTGAACTTG | 21<br>22 | NM_001101 |
| GAPDH | AAGGTCGGAGTCAACGGAT<br>GGAAGATGGTGATGGGATTTC | 23<br>24 | NM_002046 |

TABLE 3A

Identity of the proteins encoded by the differentially expressed genes (most deregulated genes).

| Gene Name | Protein Name |
|---|---|
| ACTG2 | Actin, gamma-enteric smooth muscle |
| BMP3 | Bone morphogenetic protein 3 |
| C20orf103 | Lysosome-associated membrane glycoprotein 5 |
| C4orf49 | Protein MGARP |
| C8orf84 | Somatomedin-B and thrombospondin type-1 domain-containing protein |
| CA9 | Carbonic anhydrase 9 |
| CACNA1A | Voltage-dependent P/Q-type calcium channel subunit alpha-1A |
| CCL5 | RANTES(4-68), C-C motif chemokine 5 |
| CDA | Cytidine deaminase |
| CDH2 | cDNA FLJ53252, highly similar to Cadherin-2 |
| CLEC3A | C-type lectin domain family 3 member A |
| CLU | Clusterin beta chain |
| CRTAC1 | Cartilage acidic protein 1 |
| DEFB103B | Beta-defensin 103 |
| DEFB4A | Beta-defensin 4A |
| GNAZ | Guanine nucleotide-binding protein G(z) subunit alpha |
| GPX3 | Glutathione peroxidase, Glutathione peroxidase 3 |
| GRP | Gastrin-releasing peptide |
| HEYL | Hairy/enhancer-of-split-related with YRPW motif-like protein, Hairy/enhancer-of-split related with YRPW motif-like protein |
| IL36RN | Interleukin-36 receptor antagonist protein |
| KCNE3 | Potassium voltage-gated channel subfamily E member 3, Cardiac voltage-gated potassium channel accessory subunit isoform 3b |
| KIF5C | Kinesin heavy chain isoform 5C |
| KIT | Mast/stem cell growth factor receptor Kit |
| KLK6 | Kallikrein-6 |
| KRT12 | Keratin, type I cytoskeletal 12 |
| LAMA3 | Laminin alpha-3 chain variant 2, Laminin subunit alpha-3, Laminin alpha 3 splice variant a |
| LAMC2 | Laminin subunit gamma-2 |
| LCE3D | Late cornified envelope protein 3D |
| MGP | Matrix Gla protein |
| MMP10 | Stromelysin-2 |
| MMP9 | Matrix metalloproteinase-9 |
| MYH4 | Myosin-4 |
| NPAS4 | Neuronal PAS domain-containing protein 4 |
| PAMR1 | Inactive serine protease PAMR1 |
| PI3 | Elafin |
| PLA2G16 | HRAS-like suppressor 3 |
| PTHLH | Parathyroid hormone-related protein |
| RASSF2 | Ras association domain-containing protein 2 |
| RERG | Ras-related and estrogen-regulated growth inhibitor |
| RGS4 | Regulator of G-protein-signaling 4, Regulator of G-protein signaling 4 |
| RGS5 | Regulator of G-protein signalling 5, isoform CRA_a; Regulator of G-protein-signaling 5; Regulator of G-protein signaling 5 |
| RGSL1 | Regulator of G-protein signaling protein-like, Regulator of G-protein-signaling protein-like |
| SCRG1 | Scrapie-responsive protein 1 |
| SLC13A5 | Solute carrier family 13 member 5 |
| SOX11 | Transcription factor SOX-11 |
| SPRR2B | Small proline-rich protein 2B |
| SPRR2D | Small proline-rich protein 2D |
| SPRR2G | Small proline-rich protein 2G |
| SULF1 | Extracellular sulfatase Sulf-1 |
| VCAM1 | Vascular cell adhesion protein 1 |
| WFDC12 | WAP four-disulfide core domain protein 12 |
| WFDC5 | WAP four-disulfide core domain protein 5 |

TABLE 3A-continued

Identity of the proteins encoded by the differentially expressed genes (most deregulated genes).

| Gene Name | Protein Name |
|---|---|
| ZFP42 | Zinc finger protein 42 homolog |
| ZNF853 | Zinc finger protein 853 |

TABLE 3B

Identity of the proteins encoded by the differentially expressed genes (MMP)

| Gene Name | Protein Name |
|---|---|
| MMP1 | Interstitial collagenase |
| MMP2 | PEX, 72 kDa type IV collagenase |
| MMP3 | Stromelysin-1 |
| MMP7 | Matrilysin |
| MMP8 | Neutrophil collagenase |
| MMP9 | Matrix metalloproteinase-9 |
| MMP10 | Stromelysin-2 |
| MMP11 | Stromelysin-3 |
| MMP12 | Macrophage metalloelastase |
| MMP13 | Collagenase 3 |
| MMP14 | Matrix metalloproteinase-14 |
| MMP15 | Matrix metalloproteinase-15 |
| MMP16 | Matrix metalloproteinase-16 |
| MMP17 | Matrix metalloproteinase-17 |
| MMP19 | Matrix metalloproteinase-19 |
| MMP20 | Matrix metalloproteinase-20 |
| MMP21 | Matrix metalloproteinase-21 |
| MMP23B | Matrix metalloproteinase-23, soluble form |
| MMP24 | Matrix metalloproteinase-24 |
| MMP25 | Matrix metalloproteinase-25 |
| MMP26 | Matrix metalloproteinase-26 |
| MMP27 | Matrix metalloproteinase-27 |
| MMP28 | Matrix metalloproteinase-28 |

TABLE 3C

Identity of the proteins encoded by the differentially expressed genes (cytokines and growth factors genes).

| Gene Name | Protein Name |
|---|---|
| IL1A | Interleukin-1 alpha |
| IL1B | Interleukin-1 beta |
| IL6 | Interleukin-6 |
| IL8 | Interleukin-8 |
| IL11 | Interleukin-11 |
| IL17D | Interleukin-17D |
| IL20 | Interleukin-20 |
| IL24 | Interleukin-24 |
| IL37 | Interleukin-37 |
| MEGF10 | Multiple epidermal growth factor-like domains protein 10 |
| TGFB1 | Transforming growth factor beta-1 |
| TGFB3 | Transforming growth factor, beta 3 |
| TNF | Tumor necrosis factor |

TABLE 3D

Identity of the proteins encoded by the differentially expressed genes (transcription factors genes).

| Gene Name | Protein Name |
|---|---|
| FOS | V-fos FBJ murine osteosarcoma viral oncogene homolog, isoform CRA_b; Proto-oncogene c-Fos |
| FOSB | Protein fosB |
| Fra1 | Fos-related antigen 1; cDNA FLJ51531, highly similar to Fos-related antigen 1 |
| Fra2 | Fos-related antigen 2 |
| JUN | Transcription factor AP-1 |
| JUNB | Transcription factor jun-B |
| JUND | Transcription factor jun-D |
| SP1 | Transcription factor Sp1 |
| SP3 | Transcription factor Sp3 |

Figure 2C:
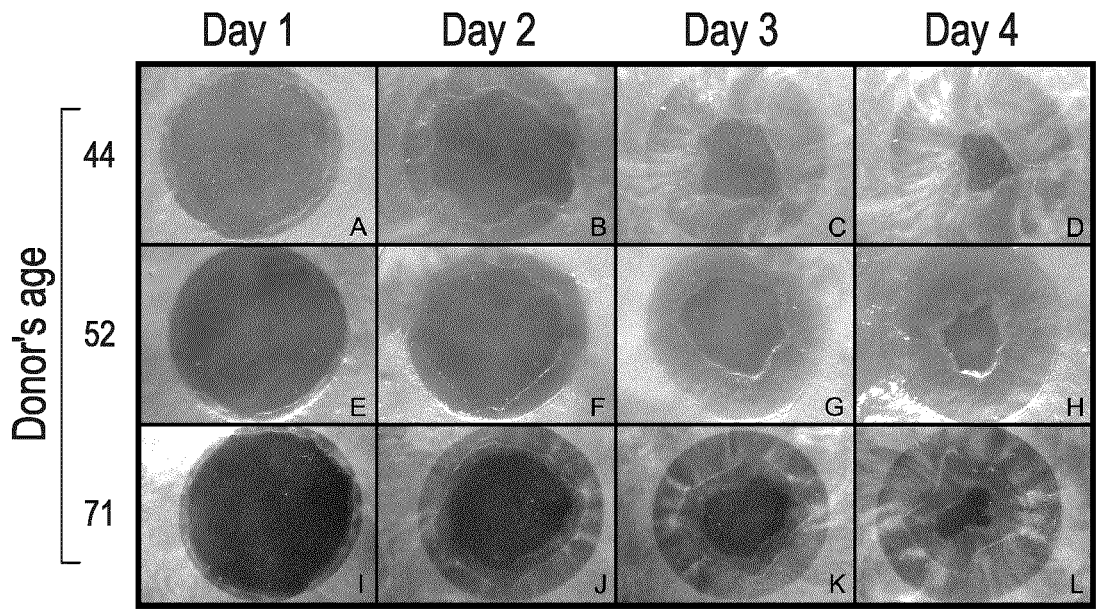
Figure 2D:
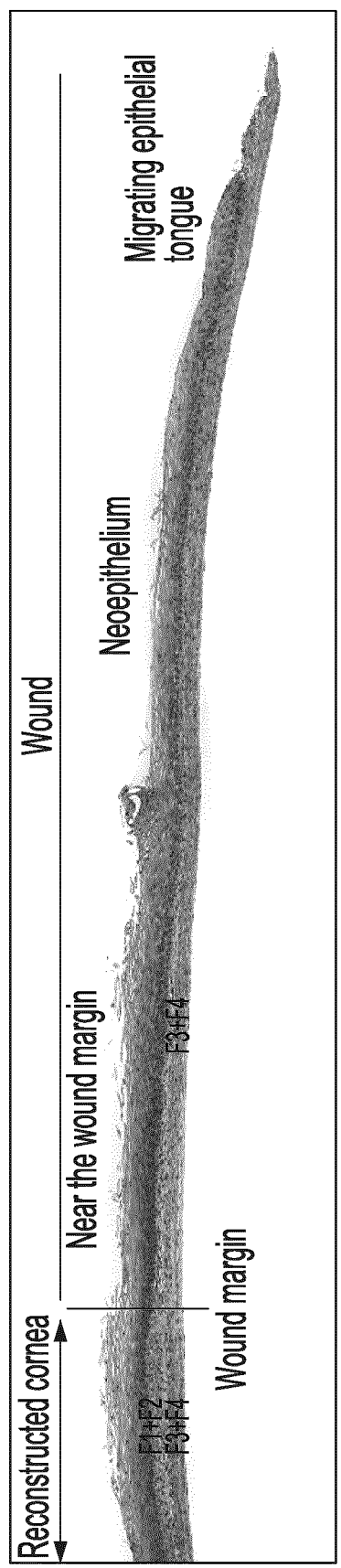

Analysis of Corneal Wound Healing in Tissue-Engineered Human Corneas. We first evaluated the feasibility of using tissue-engineered human corneas as a model for studying the molecular mechanisms of partial thickness wound healing of the anterior cornea in an environment close to the in vivo condition. As shown on FIG. 2C, macroscopic observation of wound closure in tissue-engineered, two-layers human corneas wounded using a punch biopsy revealed that migration of the corneal epithelium was unequal in each of the three independent wounded corneas. Indeed, multiple convex leading fronts from different regions of the surrounding intact epithelium advanced toward the center (FIG. 2C). These migrating fronts developed within 12 to 24 hours after wounding and continued to advance for the period studied (96 hours). Only between 6 to 10% of the wounded areas was remaining at 4 days (FIG. 2C, subpanels D, H and L) and all wounds were completely closed at 5 days (results not presented). The neoepithelium was clearly visible 3 days after wounding (FIG. 2D). Furthermore, the epithelium was stratified and similar to the normal corneal structure near the wound margin and in the middle of the neoepithelium. Therefore, the well-differentiated epithelium from the tissue-engineered corneas produced using the self-assembly approach appropriately responded to injury and demonstrated the validity of using this substitute as a model to study further the mechanisms of epithelial wound healing.

The Gene Expression Pattern is Altered by Wound Healing in the Tissue-Engineered Human Cornea. We next wounded tissue-engineered corneas and conducted gene profiling analysis on microarrays using total RNAs isolated from the epithelial cells of three different areas (central, internal and external areas) from our reconstructed tissues after 4-days of culture under air-liquid condition. A scatter plot analysis of the 60 000 different transcripts contained on the arrays indicated clearly that HCECs from the central area of wounded corneas have patterns of expressed genes distinctive from those yielded by HCECs from unwounded corneas as revealed by the dispersion of the normalized signals that appear as a cloud (data not shown) and the slope of the regression curve ($R^2$=0.9316). However, as we move away from the wounded central area toward both the internal and external rings, the number of deregulated genes progressively decreases, as is also revealed by the change in the slope of the regression curve ($R^2$=0.9362 and 0.9417, respectively). Comparison of internal and external transcriptional profiles revealed a more modest global change in the patterns of genes expressed by these cells ($R^2=0.9726$).

A heatmap for all the genes showing a 2-fold or more expression variation unique to HCECs from the central, internal and external areas of wounded corneas paired with their corresponding regions in the unwounded cornea was then generated. A total of 2754 genes fitted into that category of differentially regulated genes when HCECs from the central area are compared between wounded and unwounded corneas. The number of total genes deregulated by more than 2-fold decreased to 2626 and 2283 when the microarray data from the internal and external areas, respectively, are compared between the wounded and unwounded tissue-engineered corneas.

Figure 4A:
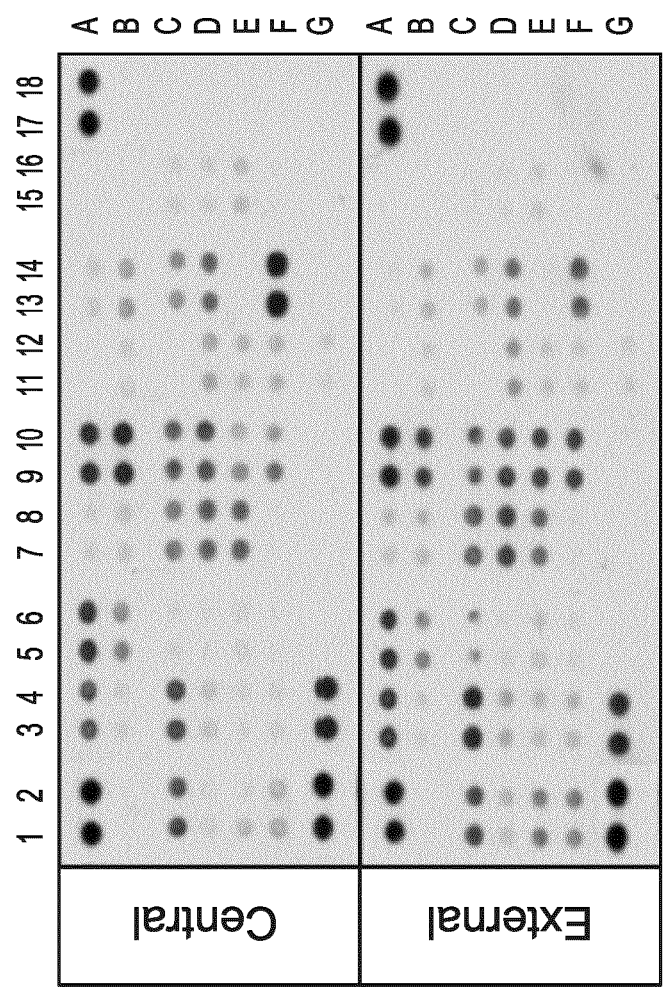
FIGS. 4A to 4C illustrate the proteome array of phosphorylated kinases and mediators in response to corneal wound healing. (A) Western blot analyses conducted using the Human Phospho-kinase Antibody Array from R&D Systems. The protein extracts used were prepared from central (wounded) and external (unwounded) areas of reconstructed human corneas. (B) Kinases and mediators identified in (A) as being differentially phosphorylated between central (wounded) and external (unwounded) areas of tissue-engineered corneas. The graph compares the densitometric analysis of each of the dot blot duplicates between central (wounded) and external (unwounded) areas of tissue-engineered corneas. (C) Heatmap (DNA microarray) that shows the expression pattern of the genes encoding the kinases and mediators shown in (B).
Figure 4B:
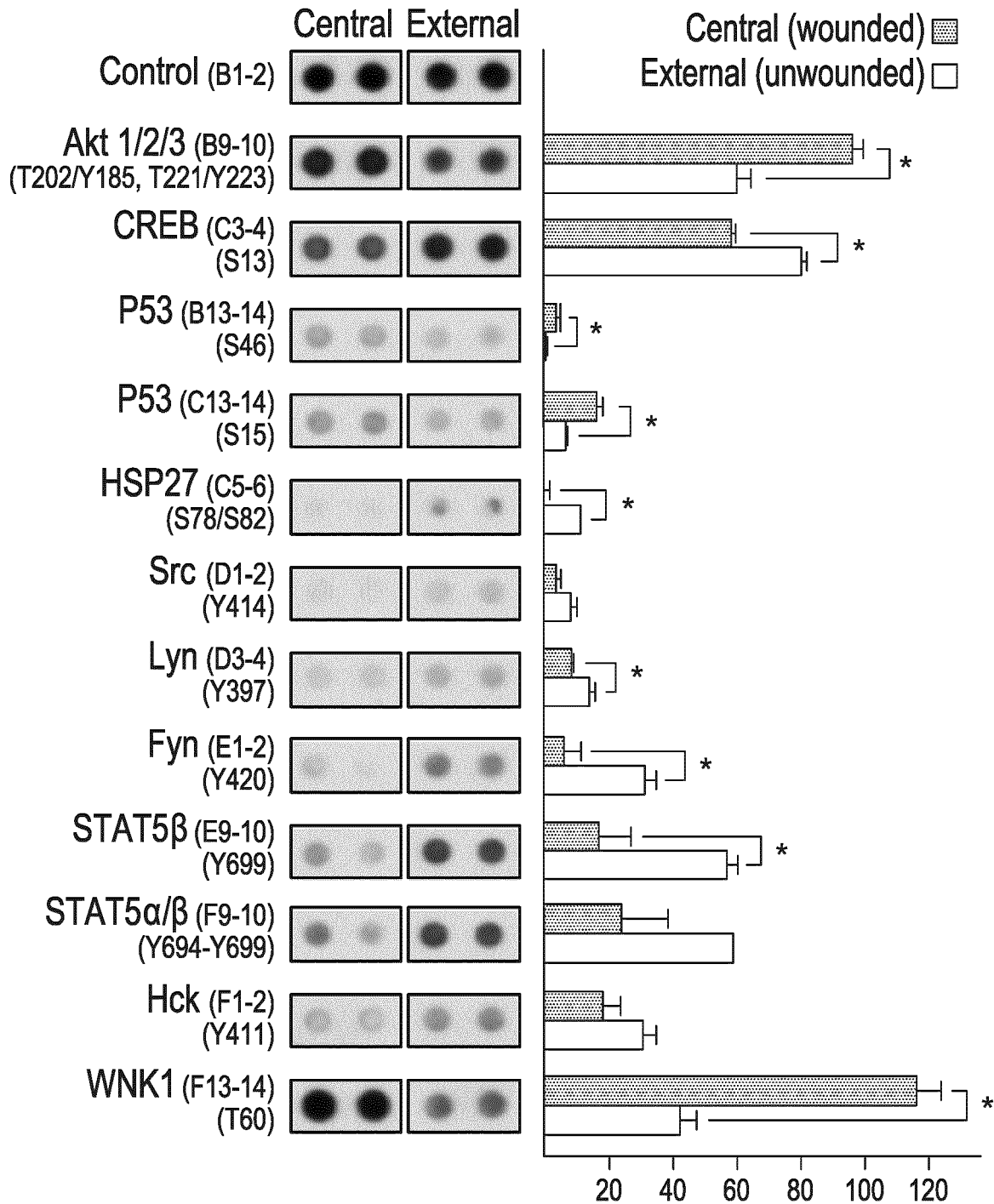
Figure 4C:
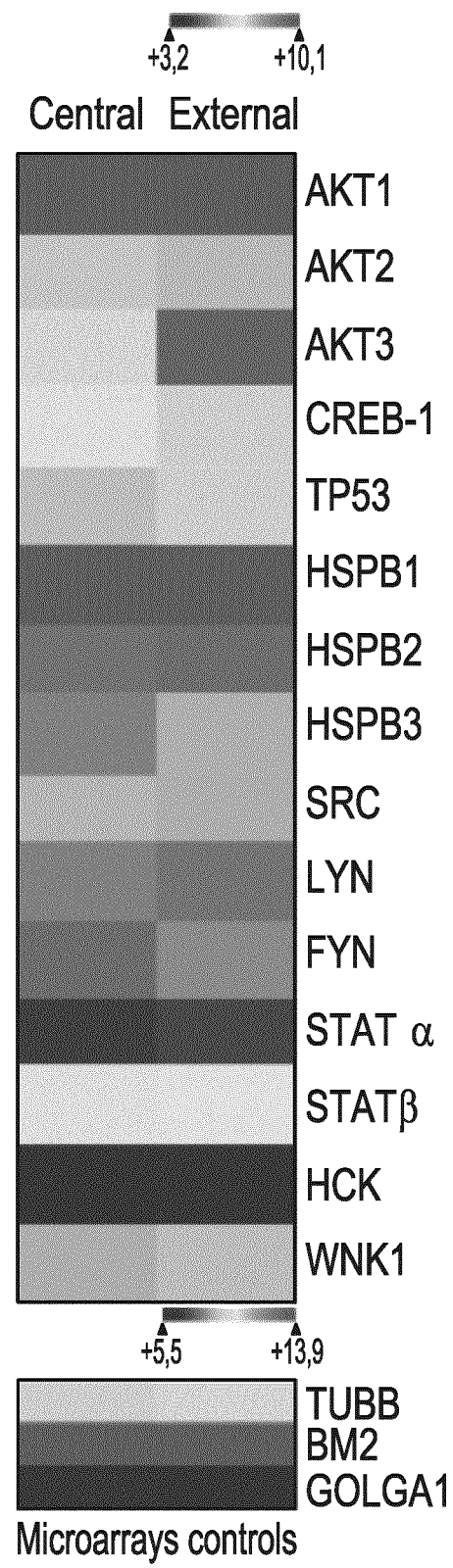

FIG. 4 shows the modulation in phosphorylation of various kinases in the wounded region (FIG. 4; central) when compared to a non-wounded region of reconstructed corneas (FIG. 4; external). More specifically, the results presented in FIG. 4 indicated that mediators of the JAK/STAT, MAPK, JNK and PI3K pathways were differentially phosphorylated in the wounded and in the non-wounded region. In addition, Akt was hyperphosphorylated in the wounded region (central region) when compared to the non-wounded region. Activity of Akt is thus involved in the corneal wound repair. On the other hand, CREB was hypophosphorylated in the wounded region (central region) when compared to the non-wounded region (external region). These results suggest that CREB is thus involved in the corneal wound repair and its inhibition would be beneficial to accelerate or favor wound healing.

We next examined the data files from the microarrays to sort out genes whose expression is the most deregulated in HCECs from the central, internal and external areas of the wounded corneas relative to their unwounded substitutes. The 55 most deregulated genes were ordered according to their variation during wound healing and arbitrarily named class I, II and III. Expression of the genes identified as class I was dramatically reduced in the central wound and remained low as we move away from the wounded area in both the internal and external rings. On the other hand, genes from class II seek their expression strongly increased in the central wound but tend to return to the level of the unwounded control as we move away from the central area. Genes from class III are heavily down-regulated in the central wound and also tend to return to their normal level in the unwounded control as we move away from the central area.

Epithelial cells respond to corneal damage by altering the expression of MMPs. As both metalloproteinases MMP9 and MMP10 were among the 55 genes identified as the most deregulated in the central area of wounded, tissue-engineered corneas, we examined whether other MMP genes had their expression altered during wound healing by searching into the microarray data files. Five additional MMPs (MMP1, MMP2, MMP3, MMP11 and MMP13), besides MMP9 and MMP10, also had their expression considerably increased in the central area of wounded, reconstructed corneas. Remarkably, expression of all of them rapidly decreases as we move away from the central wound (in both the internal and external rings). As the activity of MMPs is dependent on the TIMPs, we also monitored their expression during wound healing of the tissue-engineered corneas. Of the four TIMPs, only TIMP3 had its expression considerably increased in the central wound. With the only exception of MMP11, the increased MMPs expression observed in microarray were also validated by qPCR. Detection of MMP11 in our microarray data files is, however, consistent with previous analysis that observed expression of that gene in corneal epithelial cells.

We then examined whether the alterations observed in microarray for the expression of MMPs may have resulted from corresponding changes in the expression of interleukins and TGFβ in the central area of wounded corneas as these diffusible compounds are well documented to influence on MMPs expression through alterations in the expression and/or activity of the transcription factors Sp1 and AP-1. Indeed, dramatic increases in the central area that progressively decrease as we move away from the wounded area could be observed by microarrays for IL-1α, IL-1β, IL-6, IL-11 and both TGF-β1 and TGF-β3 expression. Interestingly, expression of the gene encoding Sp1 was lower in the central area than in the periphery of the wounds whereas that of the AP-1 constituting subunit c-Jun was considerably higher in the central wounded area. Both these results (decreased Sp1 and increased AP-1 expression) were further confirmed by qPCR. The reduced expression of the Sp1 transcript in the central wound also translated into a corresponding reduction of the Sp1 protein relative to the level observed into both the internal and external rings. Meanwhile, Western blot analyses revealed that expression of the AP-1 subunits c-Fos, c-Jun and JunB was higher in both the central and internal areas than in the external ring of wounded corneas, a result somehow consistent with both the microarray and qPCR data.

As we identified many MMPs whose expression is deregulated during wound healing of two-layers tissue-engineered corneas, we next monitored their secretion into the culture medium by Western blot during wound closure over a four-day period. All of the MMPs whose transcription was demonstrated to be deregulated in the central area of wounded corneas by microarray (MMP1, MMP2, MMP3, MMP9, MMP10, MMP11 and MMP13) were also expressed at the protein level prior to wounding although both MMP3 and MMP11 were very low (day 0). Interestingly, the amount of inactive pro-MMP1 progressively diminished with increasing wound closure time whereas that of active MMP1 increased, as is revealed by the decrease in the pro-/active MMP ratio. Similar results were also observed with MMP11. No significant change was observed in the pro-/active MMP2 ratio, which is consistent with the modest 2-fold increase observed in the MMP2 enzymatic activity. Interestingly, the amount of secreted pro-MMP9 progressively diminished as wound closure was progressing suggesting that pro-MMP9 was converted into the active form of the enzyme as wound closure proceeds. This is indeed consistent with the increased enzymatic activity observed in gel zymography for MMP9 in the culture medium of wounded reconstructed cornea (9-fold increase in gelatinolytic activity at day-4 relative to day-0). As for MMP9, our antibodies against MMP3 and MMP13 could only recognize the inactive pro-enzyme. Expression of pro-MMP3 increased at 1-day post-wounding but remained constant until 4-day wound closure. Interestingly, basal expression of the MMP1, MMP3, MMP10, MMP11 and MMP13 pro-enzymes increased within 24 h and then progressively decreased (for MMP1, MMP10 and MMP11) as wounds were closing.

Deregulated expression of MMPs by HCECs depends on the presence of stromal fibroblasts. We next wished to determine which of the fibroblasts or the ECM they secrete contributes the most to the change in the expression of MMPs secreted by HCECs during wound healing. Culturing HCECs on the stromal matrix depleted of its fibroblasts (ECM influence alone) resulted in a significant increase in the expression of many MMPs (MMP1, MMP7, MMP9, MMP10, MMP14, MMP15, MMP17 and MMP23B) relative to the pattern seen when HCECs are grown solely on BSA. These results were validated further for both MMP9 and MMP10 (which are also the most deregulated) by qPCR and gel zymography (for both MMP2 and MMP9). In addition, TIMP3 gene expression was also substantially increased in HCECs by the devitalized stroma. Remarkably, preserving the stromal fibroblasts within the tissue-engineered stroma (stroma+) dramatically increased expression of MMPs (MMP2, MMP3, MMP12, MMP13 and MMP24) that otherwise did not responded to the tissue-engineered ECM alone (stroma−). On the other hand, expression of MMP1, MMP10 and MMP14 (and also that of TIMP2) was primarily dictated by the interaction of HCECs with the secreted ECM as no further increase was observed when living fibroblasts were maintained in the stroma. Interestingly, expression of the MMP7 gene (as well as that of TIMP3), which was considerably stimulated by the ECM alone, increased further when living fibroblasts were present in the stroma suggesting that its transcription responds to both the ECM and the diffusible factors secreted by fibroblasts.

As the ECM is a complex structure made up of different cell-adhesion components, we next evaluated whether individual ECM components might have accounted for the increased expression of the MMPs (for instance MMP1, MMP7, MMP9, MMP10, MMP14, MMP15, MMP17 and MMP23B) in response to the devitalized ECM. MMP1 expression was considerably increased by CI but was strongly repressed by FN and TN. No increased expression was observed for MMP7 whose transcription was, however, repressed by both CIV and FN. Expression of MMP10 was also increased by CI but dramatically repressed by TN. No significant variation in the expression MMP14, MMP15, MMP17 and MMP23B was observed besides a weak decrease on LM for both MMP15 and MMP17. Interestingly, MMP9 expression was substantially increased by both CI and LM but repressed by TN, a result that was also confirmed by qPCR. However, these ECM component-dependent influences on the transcriptional activity of the MMP9 gene (activation by CI and LM and repression by TN) did not translate into corresponding alterations in the MMP9 enzymatic activity or in the amount of MMP9 protein despite an increase in the proMMP9/active MMP9 ratio when HCECs are grown on FN and TN (0.80 and 1.06 for FN and TN, respectively, compared to 0.20 on BSA). A substantial increase in the proMMP2/active MMP2 ratio was observed when HCECs are grown on TN (3.68 on TN compared to 1.81 on BSA) that also translated into a near 2-fold reduction in the MMP2 enzymatic activity on TN. As with TN, LM also increased the proMMP2/active MMP2 ratio (3.58 on TN compared to 1.81 on BSA). MMPs whose expression responded only to the presence of living stromal fibroblasts (MMP2, MMP3, MMP12, MMP13 and MMP24) were also unaffected by any of the individual ECM components on which HCECs were grown.

Figure 8A:
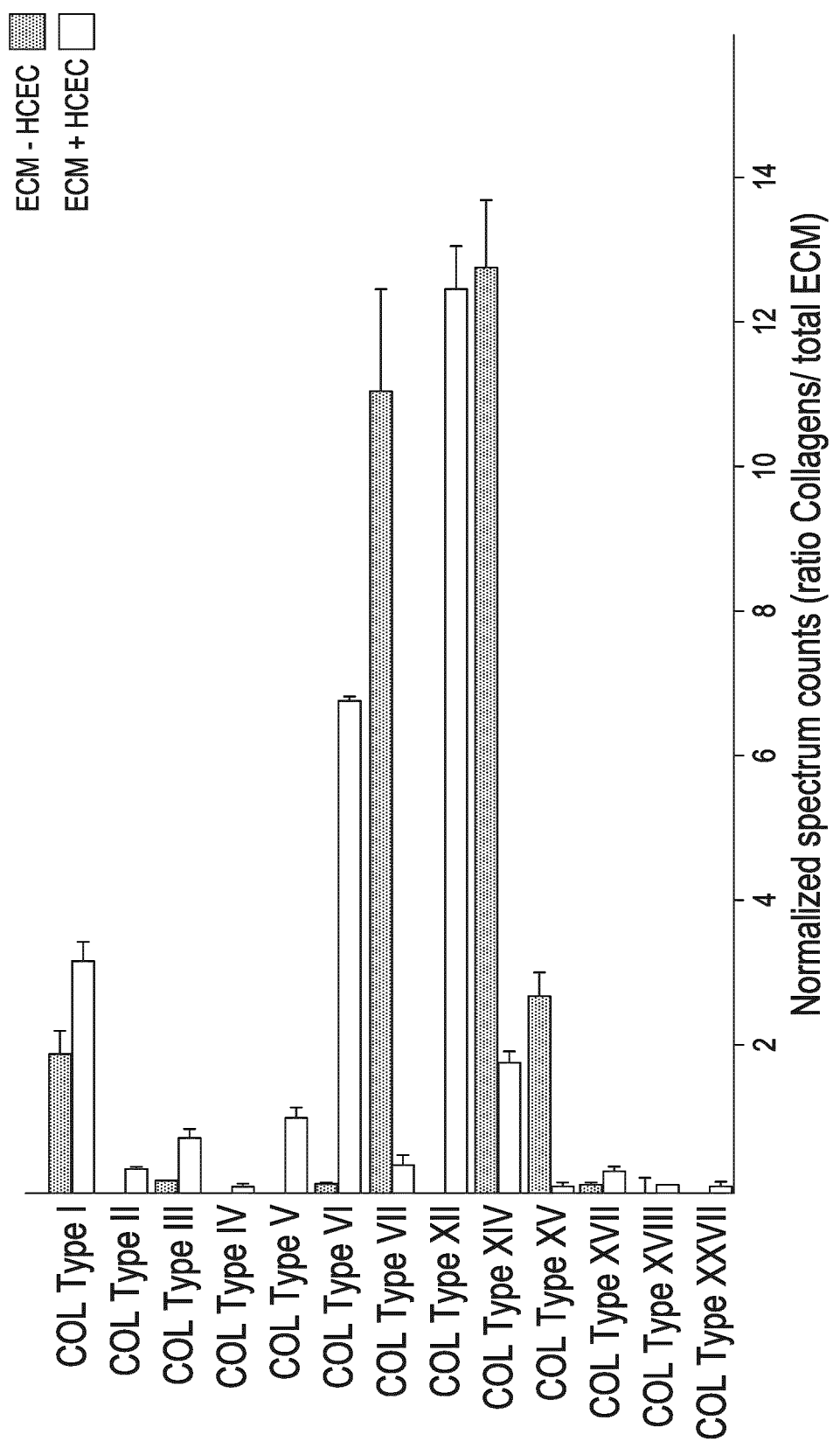
FIGS. 8A to 8C show the contribution of HCECs to the composition of the reconstructed corneal stroma. (A-C) Mass spectrometry analysis of the ECM components from the reconstructed stromas alone (stroma/HCECs−) or seeded with human corneal epithelial cells (HCECs) and then raised to the air-liquid condition in order to produce a stratified corneal epithelium (stroma/HCECs+). Data are provided for the various types of collagens (panel A), glycoproteins (panel B) and proteoglycans (panel C) (n=4). The value for each individual ECM component is expressed as the ratio of its normalized spectrum count. Results for ECM−HCEC are shown as the uppermost bar for each matrix components. Results for the ECM+HCEC are shown as the lowest bar for each matrix components.
Figure 8B:
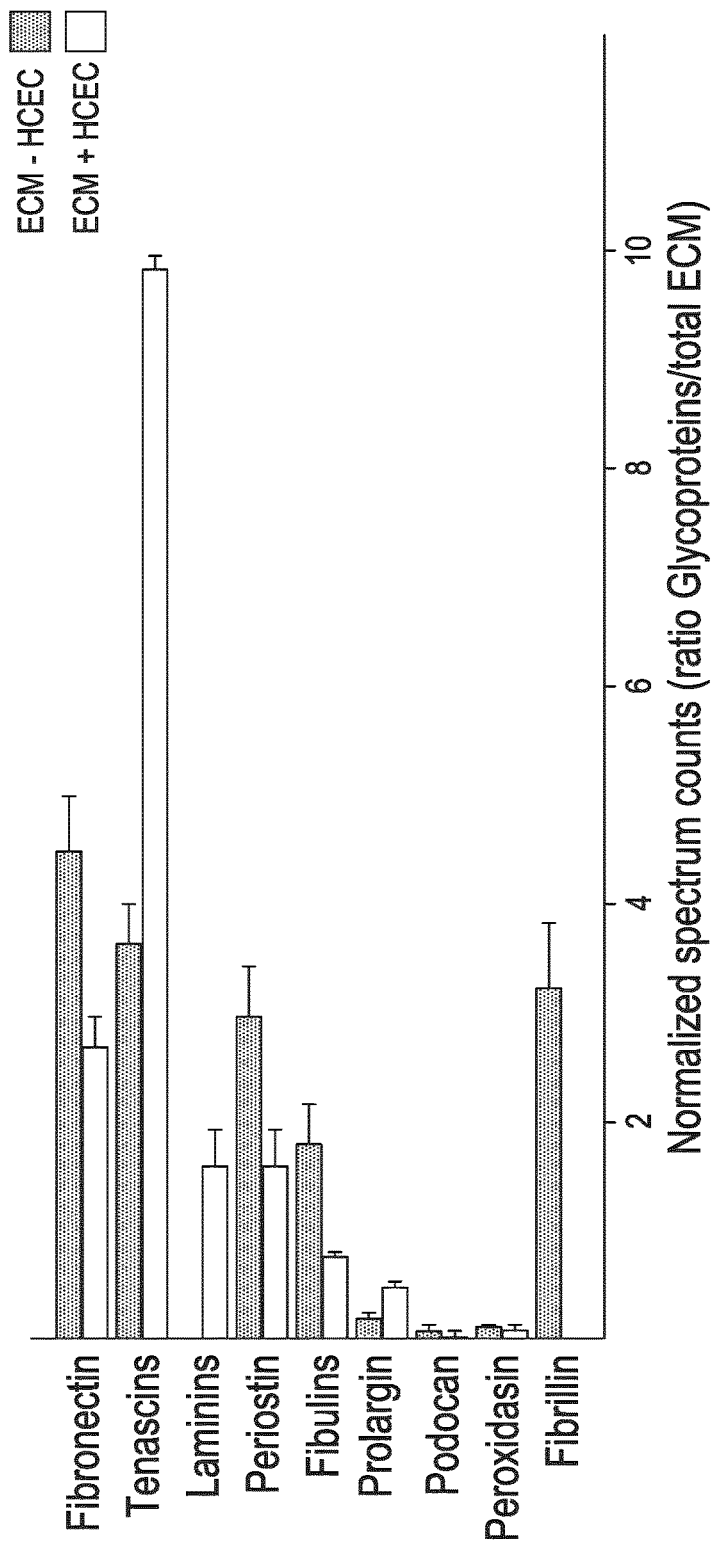
Figure 8C:
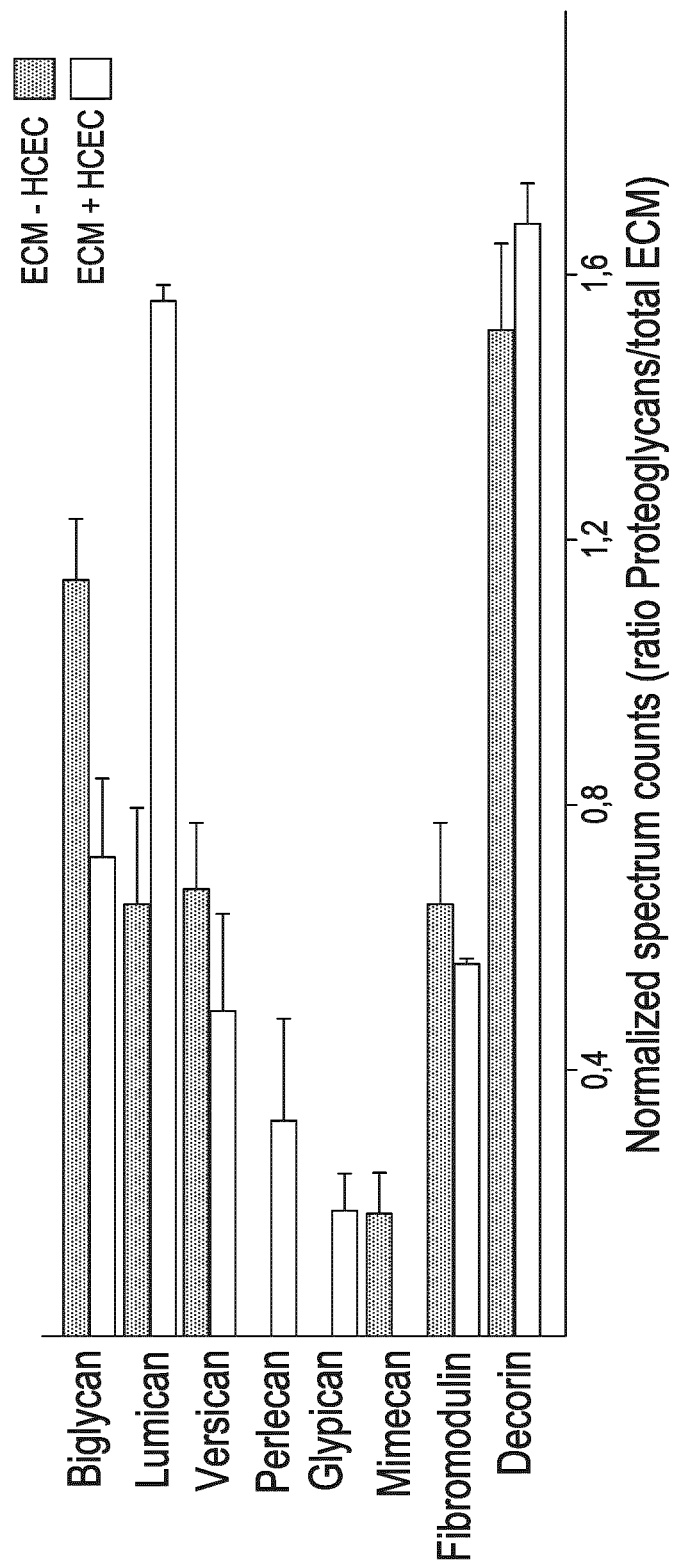

The Composition of the Stromal ECM is Under the Influence of HCECs. We next exploited mass spectrometry to determine the precise protein composition of the ECM produced by stromal fibroblasts and determined whether the presence of HCECs contributes to the final organization of this matrix. Examination of the tissue-engineered stroma that has not been added HCECs (stroma/HCEC−) revealed that it is rich in collagen types VI and XII with moderate levels of collagen types I and XIV. Altogether, collagens corresponded to 56% of all ECM peptides detected in the tissue-engineered stromas (average collagen peptides counts: 361; average total ECM peptides: 641; FIG. 8A and Table 1). Furthermore, FN, TN (that totalize 16% of the ECM components), periostin, fibulins and fibrillins are the predominant glycoproteins present in the stroma/HCEC− (FIG. 8B and Table 1) whereas low levels of the proteoglycans biglycan, lumican, versican, mimecan, fibromodulin and decorin (that altogether totalized 9% of the average total ECM peptides) could also be detected (FIG. 8C and Table 1). Addition of HCECs had little impact on the stromal accumulation of proteoglycans (11% with stroma/HCEC+ compared to 9% with stroma/HCEC− of the average total ECM peptides), besides the detection of low levels of both perlecan and glypican in the stroma/HCEC+ condition that otherwise were totally absent from the stroma/HCEC− condition (FIG. 8C). However, the presence of HCECs caused significant changes in the combination of collagens that were secreted into the stromal ECM. Indeed, the amount of collagen types-VI, -XII and XIV was considerably decreased in the stroma/HCEC+ condition whereas that of types II, III, IV, V, VII, XVII and XVIII, most of which could not be detected in stroma/HCEC−, can now be detected at low levels in stroma/HCEC+ (FIG. 8A). However, the overall proportion of collagens remained the same whether or not HCECs are present in the tissue-engineered substitutes (55% with stroma/HCEC+ compared to 56% with stroma/HCEC− of the average total ECM peptides; Table 1). Appearance of laminins, increased levels of TN and the complete disappearance of fibrillin, along with a substantial reduction in FN, periostin and fibulins are the most noticeable features occurring in the glycoproteins composition of the stroma/HCEC+. Again, despite the change in the composition of the glycoproteins when HCECs are present, their overall proportion remained the same between both conditions (34% of the average total ECM peptides for both the stroma/HCEC+ and stroma/HCEC− conditions; Table 1).

Wound healing is a well-ordered but complex process involving activities such as cell migration and proliferation. Migration of corneal epithelial cells requires the coordinated expression of growth factors and cytokines. During cell migration, the epithelial cells (and to some extent, the stromal fibroblasts as well) in turn regulate the expression of both extracellular matrix (ECM) proteins and matrix metalloproteinases (MMPs) that are required to ensure appropriate remodeling of the ECM during the wound healing process. The very fast but transitory changes occurring in the composition of the ECM on which corneal epithelial cells migrate in order to cover the damaged corneal area are probably the most important characteristic of corneal wound healing. These rapid modifications in the ECM composition are in part ensured by the enzymatic activities of MMPs whose expression and activity change as wound healing is progressing. We previously demonstrated that tissue-engineered, complex ECMs could be used as biomaterials in order to study the expression of integrin genes as well as other genes that might play a pivotal function during the corneal repair process. In the present study, we used the two layer tissue-engineered human cornea, a substitute that is much closer to the native cornea as it is constituted of a stroma and a stratified epithelium made up of 5 to 7 layers of epithelial cells, as a model system to study the contribution of MMPs to the healing of partial thickness wounds of the anterior cornea. We did not include an endothelial layer in our reconstructed cornea since the endothelium is part of the posterior cornea. It could be interesting in the future to evaluate the effect of the endothelium on wound healing since dramatic changes in the organization and quality of the corneal BM have been reported when immortalized mouse corneal endothelial cells are present in the three-dimensional corneal tissue. However, we have shown a few years ago, that endothelial cells had no influence on the composition and organization of the BM in our model. This apparent discrepancy can be explained, at least in part, by the differences between the 2 models: i) a combination of rabbit and mouse rather than human corneal cells were used and ii) rabbit corneal epithelial and stromal fibroblast cells were embedded into a collagen matrix rather than exploiting the matrix naturally secreted by the human stromal fibroblasts, as is the case in our reconstructed corneal tissues. Corneal models have also been produced with other cell types such as umbilical stem cells. It would prove interesting to use these models to evaluate the impact of a different stroma on corneal healing.

Wound healing of the injured cornea would not be possible without significant alterations in the pattern of genes expressed by the epithelial cells bordering the damaged area. Although the most dramatic change in the transcriptional pattern of deregulated genes occurs in the central wounded area (a total of 2754 genes), yet more than 2200 genes expressed by HCECs from the external ring have become deregulated by at least a 2-fold factor (1256 are commonly deregulated in both the central and external rings) despite that these cells were located far from the wounded area. Interestingly, of all these genes, 1098 were found to be deregulated in all three areas from the wounded corneas relative to their counterpart in the unwounded corneas, a clear indication that wound healing is still going on four days after wounding. These particularly interesting results suggest that the intact cells bordering the damaged area somehow transmit signals (diffusible or through cell-cell contacts) that move from cell to cell, like a wave effect, all over the intact section of the tissue-engineered cornea. In a recent study, a similar signal wave was reported to occur upon scratch injury of primary cultured cerebral cortical astrocytes. This remarkable process was demonstrated to be caused by a calcium influx from the extracellular compartment, initially triggered by the scratch wound, that is then transmitted through gap junctions to the surrounding intact cells. One of the consequences of the sudden calcium influx is the activation of the JNK/c-Jun/AP-1 pathway. Interestingly, in the present study, transcription of the c-Jun subunit encoding gene was shown to be significantly increased in the central wound (average linear signal (ALS): 548.7) and returned to the control level in the external ring (ALS: 208.9). Although scratch injury is well recognized as a model to study corneal wound healing, yet our study is the first to report the existence of such a signal wave and to examine its influence on global gene expression in a tissue-engineered, human corneal model. Alternatively, the differential gene regulatory effects we observed between the central and external areas of wounded corneas may also have resulted from cytokines and/or growth factors released in the culture media by the cells from the central wound. However, we believe this is highly improbable due to the fact that the reconstructed two-layers corneas were cultured at the air-liquid interface prior to wounding and that no culture medium was therefore present over the entire stratified corneal epithelium during wound closure, the reconstructed tissues being supplemented from their stromal compartment. Therefore, the 'signal wave' as detailed above remains a sounded possibility to explain our results.

The 55 most deregulated genes in the wounded corneas were organized into different classes (I, II and III) depending on how their expression evolves between the central, internal and external areas. Those from class I, such as VCAM1 and PAMR1, have their expression dramatically reduced in the central wound and remained low as we move away from the wounded area and never returned to their non-injured level. On the other hand, those that belong to what we defined as class II were strongly expressed in the central wound but tended to return to the level of the unwounded control as we moved away from the central area. Both MMP9 and MMP10 as well as the laminin α3 (LAMA3) and γ2 (LAMC2) genes belong to that category. Finally, those identified as class III genes suddenly became repressed in the central wound but as with the class II genes, they then tended to return to their normal control, unwounded level as we move away from the central area. No particular feature emerged from the analysis of the class I gene function. On the other hand, examination of the class II genes revealed that five of them (LAMA5, LAMC2, MMP9, MMP2 and MMP10) encodes proteins that may contribute either to the composition or the remodeling of the ECM. In addition, three genes (LCE3D, SPRR2B and SPRR2D) encodes proteins that are predominantly expressed in epithelial cells. Finally, two genes from class III (CDH2 and CRTAC1) encodes proteins that participate to cell adhesion (also refer to Table 3 for more details).

Gene profiling analysis conducted on our two-layers tissue-engineered corneas revealed often dramatic increases in the expression of the metalloproteinases-encoding genes MMP1, MMP2, MMP3, MMP9, MMP10, MMP11 and MMP13 in the central area of wounded, tissue-engineered corneal tissues, which is very similar to the pattern reported recently by Gordon et al. in a mouse corneal model of epithelial resurfacing. MMP-9 is well known to be the primary MMP synthesized and secreted by basal corneal epithelial cells that migrate to cover the wound. During rat corneal wound healing, expression of MMP1, MMP3, MMP7, MMP9 and MMP12 was also reported to increase in corneal epithelial cells. Meanwhile, wound repair after keratectomy is also characterized by increased expression of MMP1, MMP2, MMP3 and MMP9 in the rabbit and rat corneas. MMP13, along with MMP1 and MMP8, are collagenases capable of degrading native fibrillar collagens (type I, II, and III collagens). Lacking in normal control corneas, MMP13 mRNA has, however, been detected in the epithelial cells of wounded rat corneas whereas MMP10 was shown to be overexpressed in the diabetic corneal epithelium. In addition, expression of MMP3, MMP10 and MMP11, which could be detected in normal corneal epithelial cells, increases upon exposure to IL-1β and TNF-α. The pattern of MMPs expressed in our healing, partial thickness tissue-engineered corneas is therefore consistent with the metalloproteinase activities observed in various corneal pathologies that require migration or replacement of the epithelial cells.

In our biomaterial model, the presence of stromal fibroblasts clearly impacted on the MMPs secreted by HCECs (in the stroma+ condition) as they often triggered dramatic increases in the expression of MMP2, MMP3, MMP12, MMP13 and MMP24 that otherwise did not respond to the tissue-engineered ECM depleted of its fibroblasts (in the stroma– condition). It is also interesting to point out that the pattern of MMPs expressed by HCECs grown on the fibroblasts-containing stroma (Stroma+) is virtually identical to that seen in the central area of wounded partial thickness tissue-engineered corneas (Central) thereby suggesting that both the fibroblasts and the matrix they secrete are required to allow the expression of the appropriate combination of MMPs during corneal wound healing. This result clearly suggests that stromal fibroblasts do produce diffusible factors that then trigger HCECs to increase the transcription of these MMP genes as well as that of other genes whose encoded products are required for wound healing, such as integrins and ECM component encoding genes. Indeed, MMPs expression in the cornea has been shown to be modulated by cytokines (such as IL-1β and IL-6) and growth factors (such as TGFβ) through alteration in the expression and/or properties of a few transcription factors such as AP-1 and Sp1. The requirement for soluble factors secreted by living stromal fibroblasts is in agreement with our previous observation that corneal fibroblasts contribute to the differentiation and stratification properties of HCECs. Consistent with the above studies, we also identified IL-6 as one such soluble factor. Transcription of the IL-6 encoding gene was also found to increase considerably in the central wound of our partial thickness tissue-engineered corneas relative to both the internal and external rings (ALS: 576.8, 165.0 and 184.0 for central, internal and external areas, respectively). Interestingly, expression of MMP1, MMP3, MMP10, MMP11 and MMP13 has been reported to be dose dependently upregulated by IL-1β and TNF-α in corneal epithelial cells, which is also consistent with the dramatic increase in the expression of IL-1β (ALS: 316.2, 50.8 and 10.7 for central, internal and external areas, respectively) and TNF-α (ALS: 69.3, 13.9 and 16.4 for central, internal and external areas, respectively) we observed in the central area of wounded tissue-engineered corneas. Meanwhile, it was previously demonstrated clearly that TGF-β1 exerts a positive regulatory influence on the expression and production of gelatinase (MMP9), collagenases (MMP1, MMP13) and stromelysins (MMP3, MMP10, MMP11) in HCECs cultured in monolayers and suggested that TGF-β1 may play a role in the pathogenesis of MMP mediated ocular surface diseases, such as sterile corneal ulceration. This may explain at least in part the dramatic increase in the expression of MMP1, MMP2, MMP3, MMP9, MMP10, MMP11 and MMP13 that we observed in the wounded tissues of our two-layers tissue-engineered corneas as increases in the expression of both TGF-β1 (ALS: 312.6, 212.1 and 171.8 for central, internal and external areas, respectively) and TGF-β3 (ALS: 537.6, 90.3 and 68.2 for central, internal and external areas, respectively) were also observed in the central wounds relative to the controls.

One particularly unique aspect of our study is the demonstration that HCECs are required, together with stromal fibroblasts, to secrete and organize an ECM that is very close to that seen in the native cornea. This may depend in part from the inability of stromal fibroblasts to organize a typical BM without interactions with epithelial cells. The epithelial cells from the two-layers tissue-engineered human cornea were demonstrated to secrete and organize such a typical BM although its precise composition had never been precisely determined before. In the native cornea, the BM on which epithelial cells attach is enriched in various types of collagens (IV, VII, XII, XVII, XVIII), laminins (LM-111, LM-332, LM-311, LM-411, LM-511), nidogen, perlecan and small amounts of FN. With the exception of CXII and FN, none of these BM components could be detected in the tissue-engineered stroma that has not been added HCECs (stroma/HCEC−). On the other hand, they all could be detected, although at low levels, when a corneal epithelial layer was present (stroma/HCEC+), a clear indication that organization of the corneal BM do require the presence of a corneal epithelial layer. The very low level of CIV in the stroma/HCEC+ tissue-engineered corneas, which is normally present in the corneal BM and the Descemet's membrane but absent from the corneal stroma, may be accounted for by the lack of maturity of the BM beneath the stratified epithelium as a result of a rather short culture period (7 days) at the air-liquid interface. Reduced levels of CIV (as well as that of other collagen types) may also have resulted from the fact that it is a substrate of many MMPs, including MMP9 and MMP10, whose expression is dramatically increased during wound healing. Unlike for the BM components, all those from the corneal stroma, which comprise collagen types I, Ill, V, VI, XII, XIV, and various proteoglycans (decorin, lumican and mimecan) can be observed in the stroma of our tissue-engineered corneas in the absence of an epithelial layer (stroma/HCEC−). These results are also consistent with those reported in a recent study which used tissue-engineered human corneal stromas in order to examine the change in the ECM composition upon exposure of the tissue-engineered stromas to UV light. Finally, the Bowman's membrane has been shown to contain collagen types I, Ill, IV, V, VI, VII and XII (of which both CIV and CVII were thought to come from the corneal BM), all of which could be detected in the matrix from the tissue-engineered corneas grown with an epithelial layer (stroma/HCEC+).

Our results suggest that expression of LM, glypican and perlecan in the stromal and basal ECM matrix is dependent on the presence of HCECs. Laminins are normal constituents of the corneal BM and have been shown to be secreted by the basal cells (primarily LM-5) from the corneal epithelium and also suggested to be produced (for LM-10) by stromal fibroblasts. Deregulated expression of glypican has been shown to be associated with wound healing of the mouse cornea. Interestingly, perlecan, an heparin sulfate proteoglycan that cross-links many components from the ECM and cell surface molecules, is a constituent of the normal, unwounded corneal BM.

When tested individually, some of the ECM components clearly altered the pattern of MMP genes expressed by HCECs when grown as a monolayer. This was particularly noticeable for both MMP1 and MMP9. Indeed, whereas CI influenced positively the expression of both MMP1 and MMP9, TN, on the other hand, severely repressed their transcription (as well as that of MMP10). In addition, LM also increased expression of MMP9, which is consistent with the observation that silencing expression of LM alpha-4 chain also decreased MMP9 expression in extravillous explants and HTR8/SVneo cells. Furthermore, cells from human oral squamous cell carcinoma (OSCC), adenoid cystic carcinoma (CAC2) and myoepithelioma (M1) exposed to the LM alpha1 chain peptide AG73 also had increased MMP9 activity. Therefore, LM has obviously a positive influence on the expression of the MMP9 gene. However, the true significance of these alterations in the expression of MMPs by individual ECM components at the transcriptional level remains elusive as no corresponding changes were observed in the expression and enzymatic activity of these enzymes at the protein level.

EXAMPLE II

In Vitro Characterization of Activators of the AKT Pathway and Inhibitors of the MAPK Pathway in Wound Closure The wound healing of in vitro reconstructed cornea was studied. The reconstructed cornea was adapted from the methods disclosed in Carrier et al. 2008 or Example I above.

More specifically, reconstructed corneas were made and an 8-mm punch was used to create a wound in the center of the biopsy (as shown on FIG. 2A). The wounded cornea were placed on an unepitheliazed reconstructed stroma to allow the reepithelialization of the wound. During wound healing, the tested compounds were added to the culture medium at a concentration corresponding to 2× the $IC_{50}$ reported for these compounds. Wound healing was monitored daily with microphotographs. Four days after the wound healing process began, biopsies corresponding to the central, internal or external rings (see FIG. 2B) were obtained and analyzed.

Figure 3A:
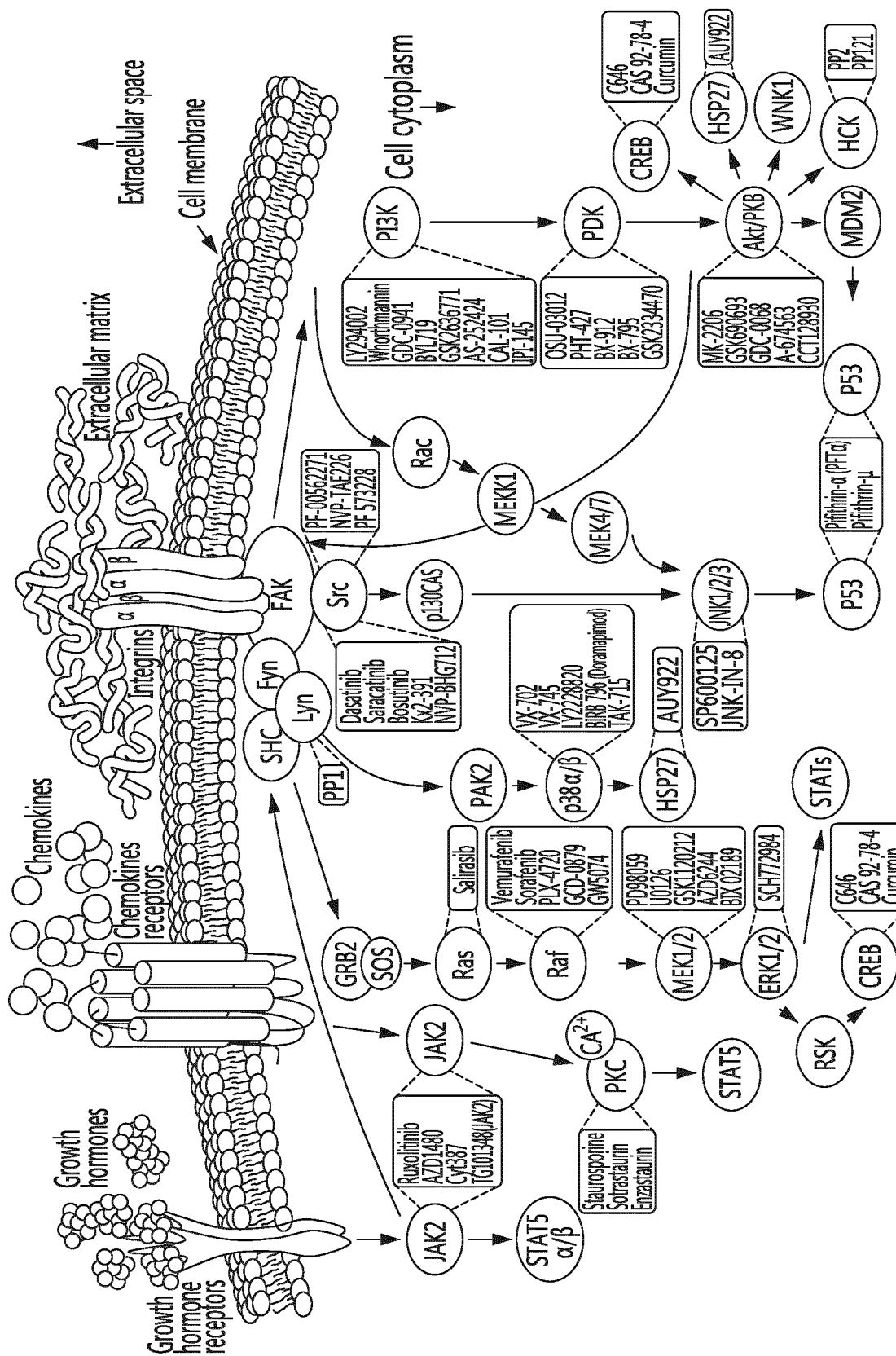
FIGS. 3A to 3B illustrate the intracellular signaling pathways activated by integrins and expression of their mediators in tissue. (A) Schematic representation of the major protein modulators that belong to the JAK/STAT, MAPK, JNK and PI3K/Akt pathways. (B) Heatmap representation of the transcriptional profiles of the most important modulators of the four signal transduction pathways (from left to right, JAK/STAT, MAPK, JNK and PI3K/Akt). The total RNAs used for these microarray analyses were prepared from the corneal epithelia isolated from the central (wounded), inner or external rings of biopsy punch-wounded tissue-engineered corneas.
Figure 3B:
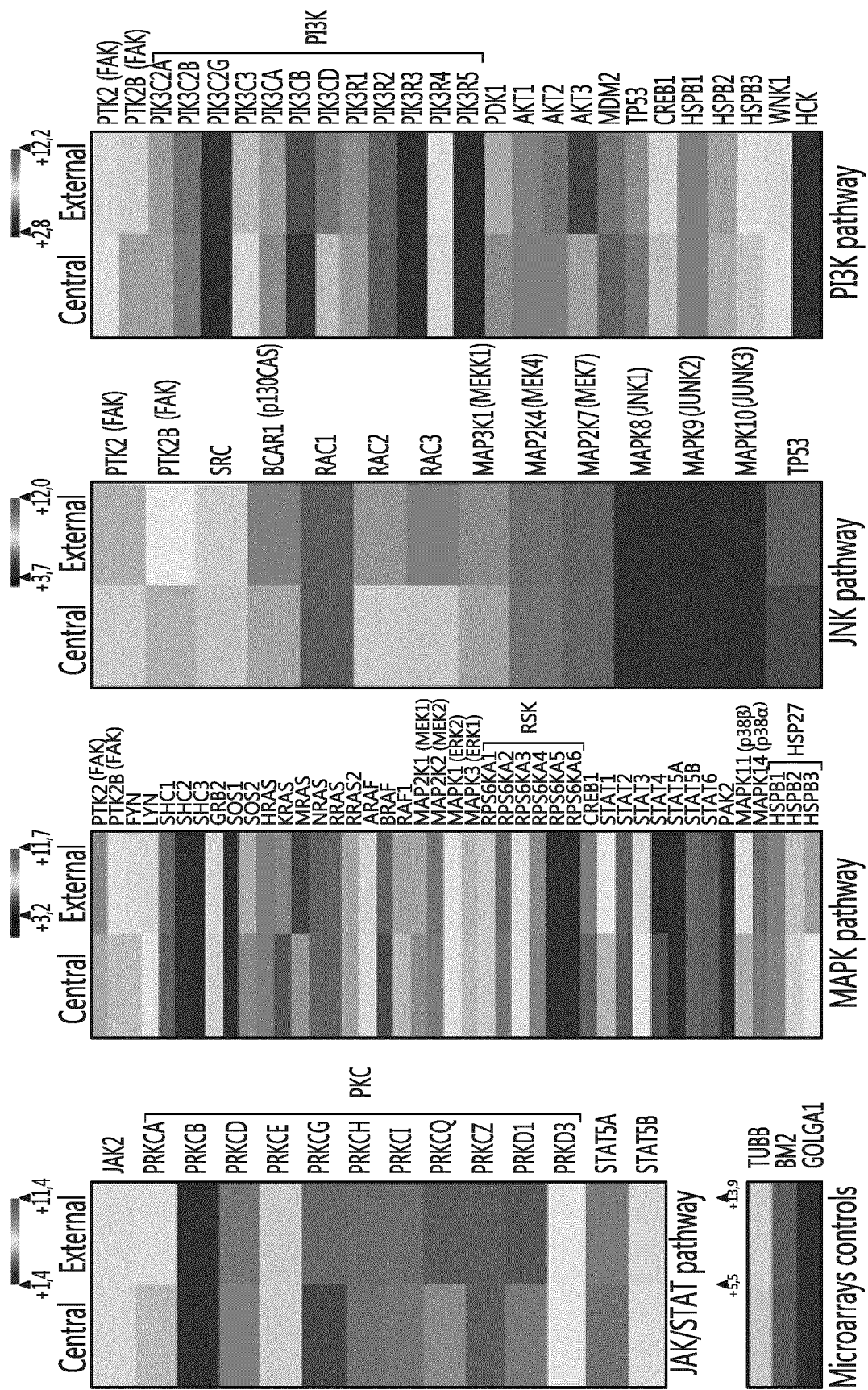
Figure 5C:
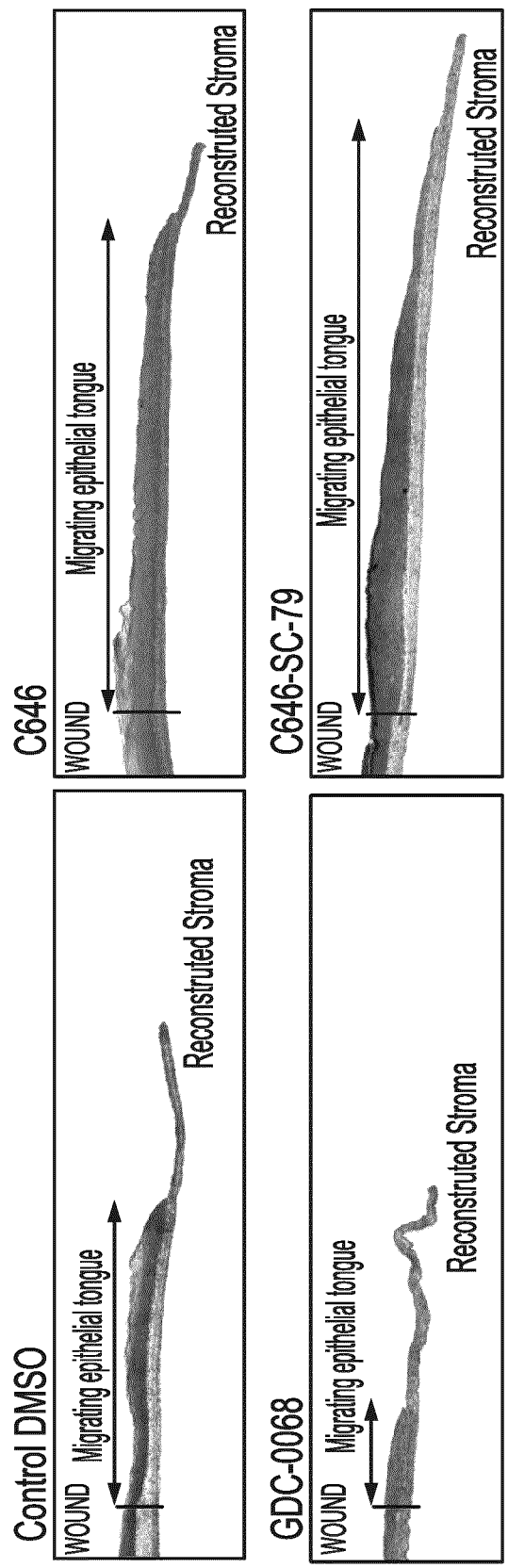

FIG. 3A shows the intracellular signaling pathways associated with integrins. The compounds used in this example either target the AKT pathway (SC-79 is an Akt activator, whereas GDC-0068 is an Akt inhibitor) or the MAPK pathway (C646 is a CREB inhibitor). As shown on FIGS. 5A and 5C, the use of an Akt inhibitor (GDC-0068) delayed wound closure when compared to control (DMSO). In clear contrast, as shown on FIGS. 5B and 5C, the use of an activator of the AKT pathway (SC-79) as well as a inhibitor of the MAPK pathway accelerated wound closure when compared to control (DMSO).

EXAMPLE III

In Vitro Characterization of Activators of the AKT Pathway and Inhibitors of the MAPK Pathway in Wound Closure Female New Zealand white rabbits (Charles River) weighing around 2 kg were used for the entire study. They were left to acclimate for 6 to 10 days prior to surgeries. Animals were injected with acepromazin 15 min. prior to isoflurane induction. Slow release Buprenorphine was then administered. Animals were then anesthesized throughout the entire surgery using 3% isoflurane inhalation. The area surrounding the treated eye was shaved, the eye washed with a chlorhexidine solution and then rinsed with 0.9% saline. One drop of alcaïne and one drop of atropine were added to the treated eye. Animals were kept on a heated blanket for the duration of the surgery.

Surgical Procedure. An 8-mm trepan was used to create a circular lesion at the surface of the rabbit corneas. One eye (left eyes) from each rabbit was used. In the first experiment, the trepan was left in place and 50 µl of either saline buffer (pH 7.4), ethanol or N-heptanol was added for 30 sec. before it was removed and the cornea washed with saline buffer. Then the epithelium was removed with a scalpel equipped with a crescent blade. In the results presented in FIGS. 6 and 7, ethanol was used for completion of the entire protocols in order to remove all residual epithelial cells. After surgery, animals were administered rheumocan (a non-steroidal anti-inflammatory compound). A second dose of rheumocan was administered 24 hours after surgery and maintained for the following days only if required.

Figure 6A:
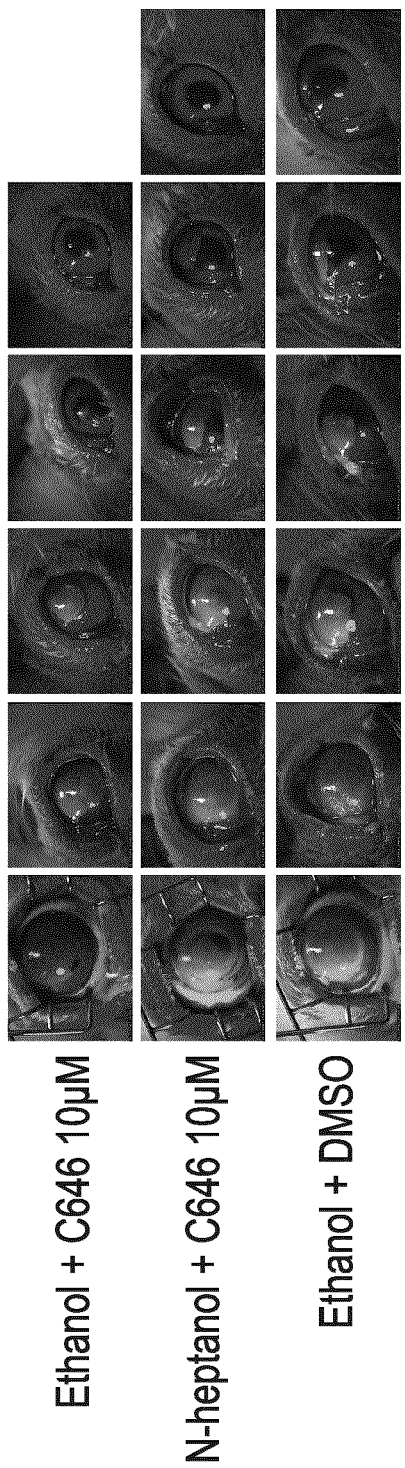
FIGS. 6A and 6B illustrate the impact of C646 on rabbit corneas wounded with either ethanol or N-heptanol combined to mechanical debridement. Rabbit corneas were wounded with ethanol (70%) or N-heptanol (100%) and mechanically debrided with a scalpel blade (crescent type). The rabbits were then divided into two groups: control corneas treated with DMSO or corneas treated with C646 (10 µm). n=4 for each conditions tested. (A) Fluorescein staining of corneas surgically wounded using either ethanol or N-heptanol combined with debridement using a crescent blade and treated with 10 µM C646. Wounded eyes were photographed using a slit lamp. (B) Graph representation of the remaining wounded corneal area (%) for each condition used in (A).
Figure 6B:
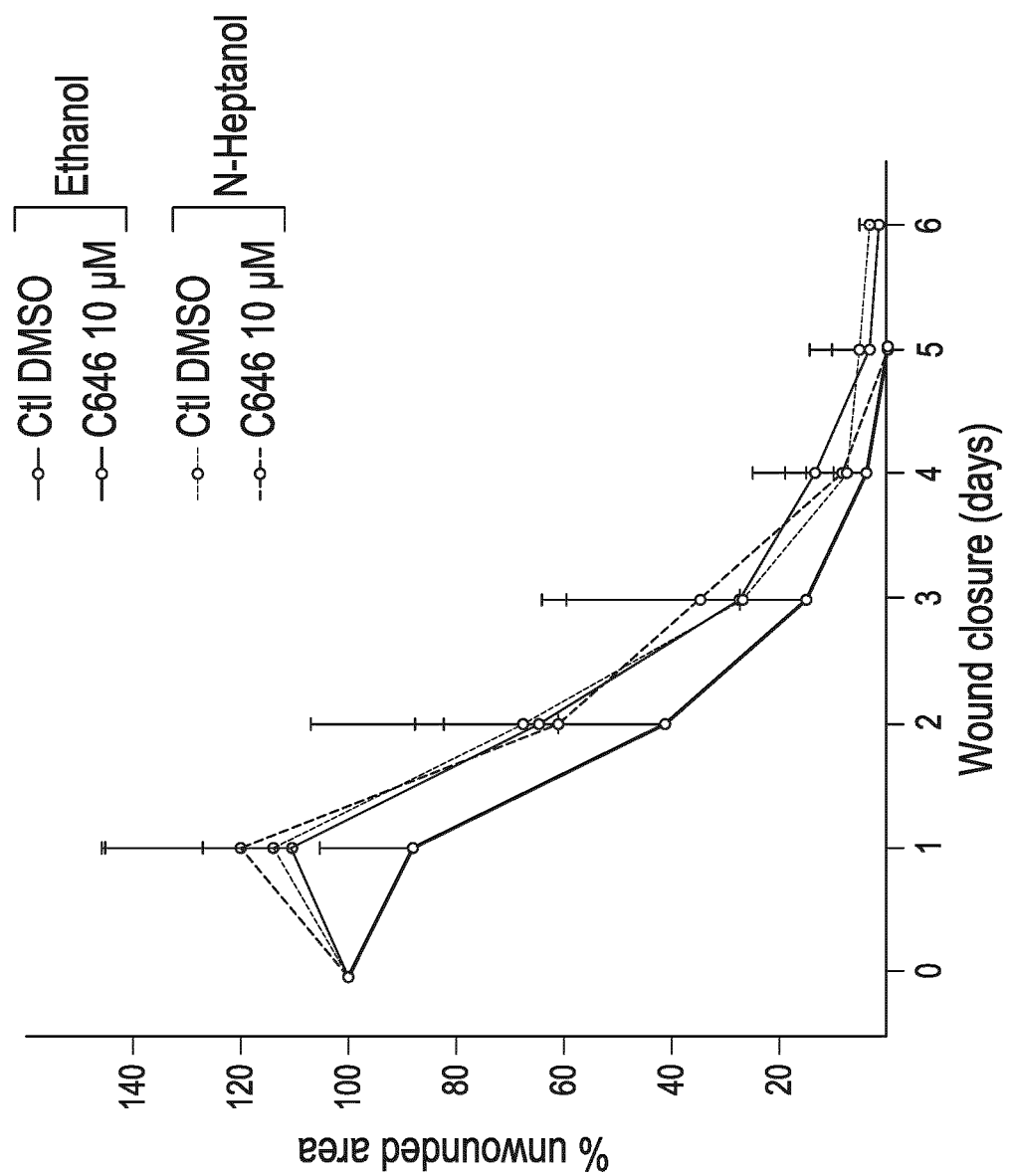
Figure 7A:
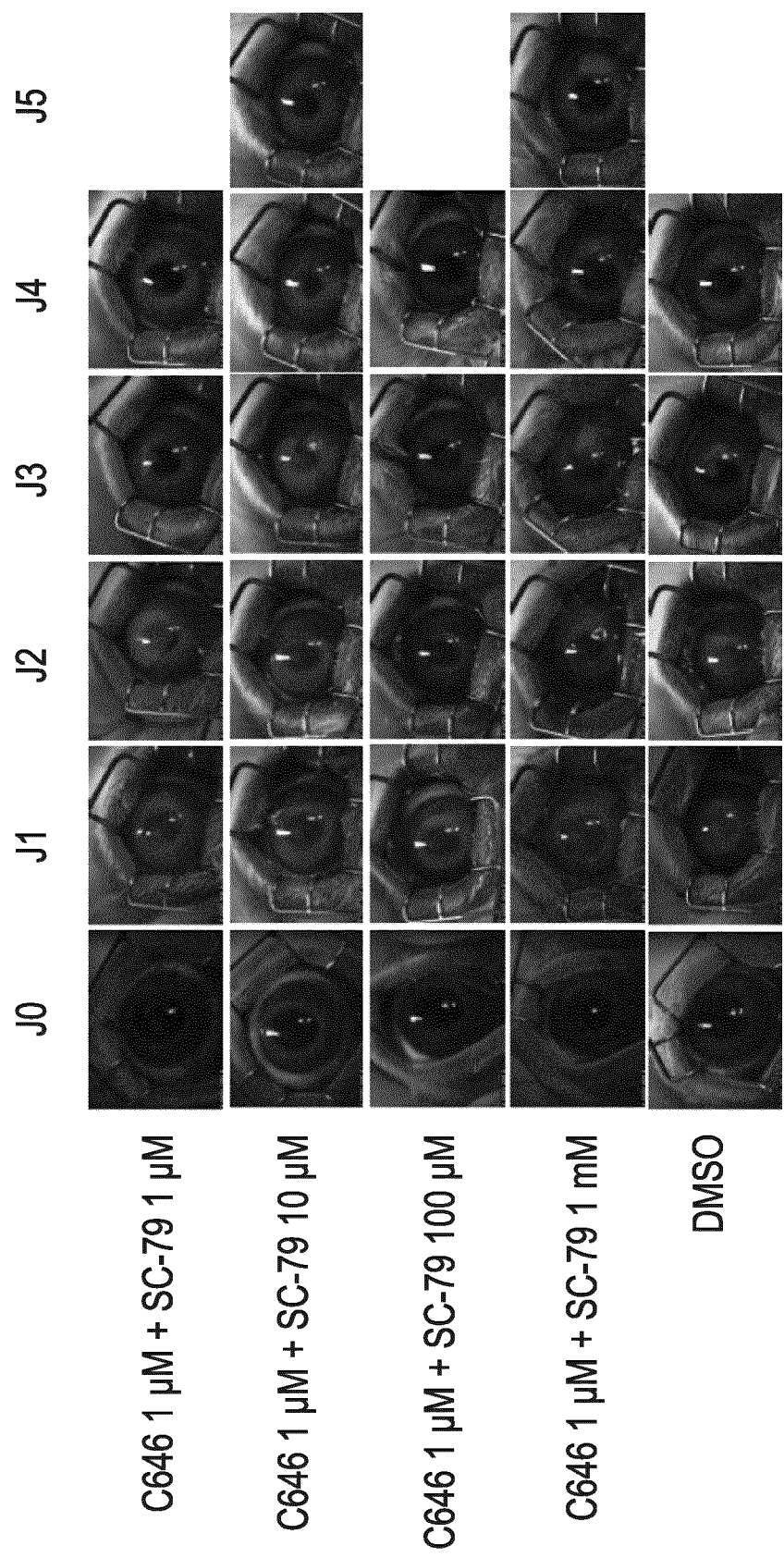
FIGS. 7A and 7B illustrate the impact of C646+SC79 on wounded rabbit corneas combined to mechanical debridement. Rabbit corneas were wounded with ethanol (70%) and mechanically debrided with a scalpel blade (crescent type). The rabbits were then divided into five groups: control corneas treated with DMSO, corneas treated with C646 (1 µM) and SC-79 (1 µM), corneas treated with C646 (1 µM) and SC-79 (10 µM), corneas treated with C646 (1 µM) and SC-79 (100 µM) and corneas treated with C646 (1 µm) and SC-79 (1 mM). n=4 for DMSO and n=5 for each remaining conditions tested. (A) Fluorescein staining of corneas surgically wounded using ethanol combined with debridement using a crescent blade and treated with a single dose of C646 (1 µM) and increasing doses of SC79 (1 µM to 1 mM). Wounded eyes were photographed using a slit lamp. (B) Graph representation of the remaining wounded corneal area (%) for each condition used in (A).
Figure 7B:
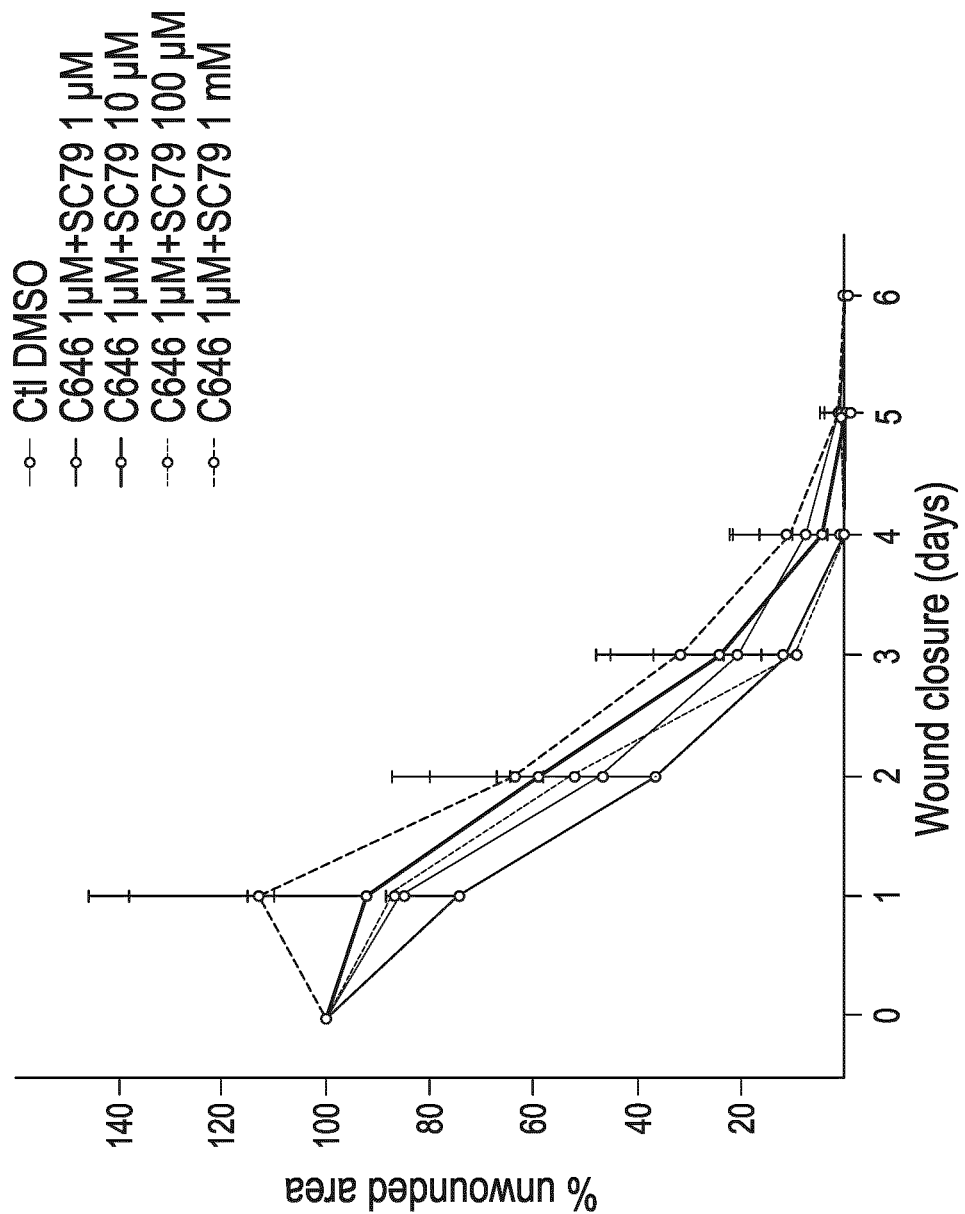

Wound Closure Protocol. In the first experiment, a single dose (10 µM) of C646 was applied 3-times/day to the wounded eyes along with erythromycin (antibiotic) until complete closure of the wounds (FIG. 6). This first experiment was very important as it allow for testing the injury model and to ensure that the corneal epithelium was differentiating and stratifying normally. For the subsequent experiment, corneal wounds were created as described above but using a combination of a single dose of C646 and increasing concentrations of SC79, along with the antibiotic, three times a day until complete closure of the wounds (FIG. 7). Saline buffer containing the vehicle (DMSO) were added 3-times/day to wounded rabbit corneas as a negative control, along with the antibiotic. pH of each solution was adjusted to 7.4 to avoid eye tearing. The wounded corneas were stained with 2% fluorescein in order to demarcate the wound margins and evaluate corneal neovascularization, and each wounded cornea then photographed every 24 hours using a slit lamp until complete closure of the wounds. Surgical retractors together with a drop of alcain have been used to maintain the rabbit eye opened during photography. Wound dimensions were measured from each photograph and at each day using the AxioVisionRel.4.8 program. One rabbit per condition was euthanized and the wounded cornea isolated, fixed in 10% formaldehyde and paraffin-embedded. Sections were prepared and stained with hematoxillin-eosin (H&E) prior to microscopic examination. All animals were euthanized by euthanyl injection in the ear's marginal vein.

As shown on FIG. 6, treating the rabbit corneas wounded using n-heptanol combined with the mechanical debridement with C646 had no significant impact on wound closure (compare the two lines associated with n-heptanol injury). However, a clear reduction in the wound closing time was observed when C646 was added to corneas wounded with ethanol combined to the mechanical debridement (compare the two lanes associated with ethanol injury).

As shown on FIG. 7, the only condition that resulted in a reduced wound closure time was the combination of 1 µM C646 together with 1 µM SC79. Higher concentrations of SC79 had either no impact or even delayed wound closure time.

While the invention has been described in connection with specific embodiments thereof, it will be understood that the scope of the claims should not be limited by the preferred embodiments set forth in the examples, but should be given the broadest interpretation consistent with the description as a whole.

REFERENCES

Boisselier E, Salmon L, Ruiz J, Astruc D. How to very efficiently functionalize gold nanoparticles by "click" chemistry. Chem Commun (Camb). 2008 Nov. 30; (44): 5788-90.

Carrier P, Deschambeault A, Talbot M, Giasson C J, Auger F A, Guerin S L, Germain L. Characterization of wound reepithelialization using a new human tissue-engineered corneal wound healing model. Invest Ophthalmol Vis Sci. 2008 April; 49(4):1376-85.

What is claimed is:

1. A method of favoring healing of an epithelial wound located in a cornea of a subject, said method comprising contacting a wound healing efficient amount of a pharmaceutical composition with the corneal epithelial wound, wherein the pharmaceutical composition comprises (i) SC-79 and (ii) C646 in combination with a pharmaceutically acceptable carrier.

2. The method of claim 1, wherein the subject is a mammal.

3. The method of claim 2, wherein the mammal is a human.

4. A method for determining the usefulness of a test compound to favor wound healing of a corneal epithelial wound, said method comprising:
   (a) contacting the test compound with a first corneal epithelial cell to obtain a treated corneal epithelial cell;
   (b) determining, in the treated corneal epithelial cell, if the test compound activates the AKT pathway and inhibits the MAPK pathway; and
   (c) characterizing the test compound as useful for favoring wound healing of the corneal epithelial wound when it is determined that the test compound activates, in the treated corneal epithelial cell, the AKT pathway and inhibits, in the treated epithelial cell, the MAPK pathway.

5. The method of claim 4, comprising determining if the test compound activates AKT gene to determine if the test compound activates the AKT pathway.

6. The method of claim 4, comprising determining if the test compounds inhibits CREB to determine if the test compound inhibits the MAPK pathway.

7. The method of claim 4, wherein the corneal epithelial cell is located in an in vitro cornea model.

8. The method of claim 7, wherein the in vitro cornea model comprises cultured keratocytes, cultured epithelial corneal cells and an extracellular matrix substantially produced by the cultured keratocytes and the cultured epithelial corneal cells.

9. The method of claim 7, wherein the in vitro cornea model is wounded before step (a) and the method further comprises determining the rate of closure of the wound in the presence of the test compound to confirm the usefulness of the test compound in favoring wound healing.

10. The method of claim 9, wherein the in vitro cornea model further comprises a second reconstructed stroma comprising cultured keratocytes and the extracellular matrix substantially produced by the cultured keratocytes placed on one side of the wound to provide support for the reepithelialization of the wound.

* * * * *

SEQUENCE LISTING

<160> NUMBER OF SEQ ID NOS: 24

<210> SEQ ID NO 1
<211> LENGTH: 21
<212> TYPE: DNA
<213> ORGANISM: Artificial Sequence

```
<220> FEATURE:
<223> OTHER INFORMATION: Oligonucleotide

<400> SEQUENCE: 1
gggcttttga tgtaccctag c                                              21

<210> SEQ ID NO 2
<211> LENGTH: 21
<212> TYPE: DNA
<213> ORGANISM: Artificial Sequence
<220> FEATURE:
<223> OTHER INFORMATION: Oligonucleotide

<400> SEQUENCE: 2
tgtcacacgc ttttggggtt t                                              21

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide

<400> SEQUENCE: 3
tagcagagcc tagacaaggg                                                20

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide

<400> SEQUENCE: 4
caggacagag ggactagagc                                                20

<210> SEQ ID NO 5
<211> LENGTH: 21
<212> TYPE: DNA
<213> ORGANISM: Artificial Sequence
<220> FEATURE:
<223> OTHER INFORMATION: Oligonucleotide

<400> SEQUENCE: 5
gtcacttgtc tgttgcacac g                                              21

<210> SEQ ID NO 6
<211> LENGTH: 21
<212> TYPE: DNA
<213> ORGANISM: Artificial Sequence
<220> FEATURE:
<223> OTHER INFORMATION: Oligonucleotide

<400> SEQUENCE: 6
agggaacttg agcgtgaatc t                                              21

<210> SEQ ID NO 7
<211> LENGTH: 18
<212> TYPE: DNA
<213> ORGANISM: Artificial Sequence
<220> FEATURE:
<223> OTHER INFORMATION: Oligonucleotide

<400> SEQUENCE: 7
gacgggtatc ccttcgac                                                  18
```

<210> SEQ ID NO 8
<211> LENGTH: 18
<212> TYPE: DNA
<213> ORGANISM: Artificial Sequence
<220> FEATURE:
<223> OTHER INFORMATION: Oligonucleotide

<400> SEQUENCE: 8
ccgagttgga accacgac                                                18

<210> SEQ ID NO 9
<211> LENGTH: 19
<212> TYPE: DNA
<213> ORGANISM: Artificial Sequence
<220> FEATURE:
<223> OTHER INFORMATION: Oligonucleotide

<400> SEQUENCE: 9
gctctgccta tcctctgag                                               19

<210> SEQ ID NO 10
<211> LENGTH: 19
<212> TYPE: DNA
<213> ORGANISM: Artificial Sequence
<220> FEATURE:
<223> OTHER INFORMATION: Oligonucleotide

<400> SEQUENCE: 10
cacatccttt tcgaggttg                                               19

<210> SEQ ID NO 11
<211> LENGTH: 19
<212> TYPE: DNA
<213> ORGANISM: Artificial Sequence
<220> FEATURE:
<223> OTHER INFORMATION: Oligonucleotide

<400> SEQUENCE: 11
ccgcaaccga cagaagagg                                               19

<210> SEQ ID NO 12
<211> LENGTH: 21
<212> TYPE: DNA
<213> ORGANISM: Artificial Sequence
<220> FEATURE:
<223> OTHER INFORMATION: Oligonucleotide

<400> SEQUENCE: 12
atcgctccat acccttaggg c                                            21

<210> SEQ ID NO 13
<211> LENGTH: 21
<212> TYPE: DNA
<213> ORGANISM: Artificial Sequence
<220> FEATURE:
<223> OTHER INFORMATION: Oligonucleotide

<400> SEQUENCE: 13
ccagacttca cgatggcatt g                                            21

<210> SEQ ID NO 14
<211> LENGTH: 19
<212> TYPE: DNA
<213> ORGANISM: Artificial Sequence
<220> FEATURE:
<223> OTHER INFORMATION: Oligonucleotide

```
<400> SEQUENCE: 14
ccgcaaccga cagaagagg                                              19

<210> SEQ ID NO 15
<211> LENGTH: 21
<212> TYPE: DNA
<213> ORGANISM: Artificial Sequence
<220> FEATURE:
<223> OTHER INFORMATION: Oligonucleotide

<400> SEQUENCE: 15
gtccctaagt aagtttcttc c                                           21

<210> SEQ ID NO 16
<211> LENGTH: 16
<212> TYPE: DNA
<213> ORGANISM: Artificial Sequence
<220> FEATURE:
<223> OTHER INFORMATION: Oligonucleotide

<400> SEQUENCE: 16
ggaggctaca gactac                                                 16

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide

<400> SEQUENCE: 17
gctggtgcat tacagagagg                                             20

<210> SEQ ID NO 18
<211> LENGTH: 19
<212> TYPE: DNA
<213> ORGANISM: Artificial Sequence
<220> FEATURE:
<223> OTHER INFORMATION: Oligonucleotide

<400> SEQUENCE: 18
ctccggaaga ggtaaggac                                              19

<210> SEQ ID NO 19
<211> LENGTH: 17
<212> TYPE: DNA
<213> ORGANISM: Artificial Sequence
<220> FEATURE:
<223> OTHER INFORMATION: Oligonucleotide

<400> SEQUENCE: 19
gggcatgtgc tgtgacc                                                17

<210> SEQ ID NO 20
<211> LENGTH: 17
<212> TYPE: DNA
<213> ORGANISM: Artificial Sequence
<220> FEATURE:
<223> OTHER INFORMATION: Oligonucleotide

<400> SEQUENCE: 20
cataagcaaa ggccatc                                                17

<210> SEQ ID NO 21
```

```
<211> LENGTH: 19
<212> TYPE: DNA
<213> ORGANISM: Artificial Sequence
<220> FEATURE:
<223> OTHER INFORMATION: Oligonucleotide

<400> SEQUENCE: 21
caagatgaga ttggcatgg                                                    19

<210> SEQ ID NO 22
<211> LENGTH: 18
<212> TYPE: DNA
<213> ORGANISM: Artificial Sequence
<220> FEATURE:
<223> OTHER INFORMATION: Oligonucleotide

<400> SEQUENCE: 22
ggccacattg tgaacttg                                                     18

<210> SEQ ID NO 23
<211> LENGTH: 19
<212> TYPE: DNA
<213> ORGANISM: Artificial Sequence
<220> FEATURE:
<223> OTHER INFORMATION: Oligonucleotide

<400> SEQUENCE: 23
aaggtcggag tcaacggat                                                    19

<210> SEQ ID NO 24
<211> LENGTH: 21
<212> TYPE: DNA
<213> ORGANISM: Artificial Sequence
<220> FEATURE:
<223> OTHER INFORMATION: Oligonucleotide

<400> SEQUENCE: 24
ggaagatggt gatgggattt c                                                 21
```